United States Patent
Galimberti et al.

(10) Patent No.: US 12,320,059 B2
(45) Date of Patent: Jun. 3, 2025

(54) ADDUCTS BETWEEN CARBON ALLOTROPES AND PYRROLE DERIVATIVES, ELASTOMER MIXTURES COMPRISING THEM AND TYRES COMPRISING SUCH MIXTURES

(71) Applicant: PIRELLI TYRE S.p.A., Milan (IT)

(72) Inventors: Maurizio Stefano Galimberti, Milan (IT); Vincenzina Barbera, Milan (IT); Gea Prioglio, Milan (IT); Luca Giannini, Milan (IT)

(73) Assignee: PIRELLI TYRE S.p.A., Milan (IT)

( * ) Notice: Subject to any disclaimer, the term of this patent is extended or adjusted under 35 U.S.C. 154(b) by 845 days.

(21) Appl. No.: 17/594,787

(22) PCT Filed: Nov. 5, 2019

(86) PCT No.: PCT/IB2019/059473
§ 371 (c)(1),
(2) Date: Oct. 29, 2021

(87) PCT Pub. No.: WO2020/225595
PCT Pub. Date: Nov. 12, 2020

(65) Prior Publication Data
US 2022/0213035 A1   Jul. 7, 2022

(51) Int. Cl.
| | | |
|---|---|---|
| C09C 1/44 | (2006.01) | |
| C01B 32/15 | (2017.01) | |
| C01B 32/20 | (2017.01) | |
| C07D 207/325 | (2006.01) | |
| C07D 513/02 | (2006.01) | |
| C07D 513/12 | (2006.01) | |
| C08J 5/24 | (2006.01) | |
| C08K 5/3415 | (2006.01) | |
| C08K 5/378 | (2006.01) | |
| C08K 5/46 | (2006.01) | |
| C08K 9/04 | (2006.01) | |
| C09C 1/48 | (2006.01) | |
| D06M 11/74 | (2006.01) | |
| D06M 13/352 | (2006.01) | |
| B82Y 30/00 | (2011.01) | |
| B82Y 40/00 | (2011.01) | |
| D06M 101/00 | (2006.01) | |

(52) U.S. Cl.
CPC ........... *D06M 13/352* (2013.01); *C01B 32/15* (2017.08); *C01B 32/20* (2017.08); *C07D 207/325* (2013.01); *C07D 513/02* (2013.01); *C07D 513/12* (2013.01); *C08J 5/244* (2021.05); *C08J 5/248* (2021.05); *C08K 5/3415* (2013.01); *C08K 5/378* (2013.01); *C08K 5/46* (2013.01); *C09C 1/48* (2013.01); *D06M 11/74* (2013.01); *B82Y 30/00* (2013.01); *B82Y 40/00* (2013.01); *D06M 2101/005* (2013.01)

(58) Field of Classification Search
None
See application file for complete search history.

(56) References Cited

U.S. PATENT DOCUMENTS

| | | |
|---|---|---|
| 2009/0036579 A1 | 2/2009 | Belin et al. |
| 2015/0191579 A1 | 7/2015 | Wampler et al. |
| 2017/0275169 A1 | 9/2017 | Galimberti et al. |

FOREIGN PATENT DOCUMENTS

| | | |
|---|---|---|
| CN | 107108220 A | 8/2017 |
| EP | 3 209 604 B1 | 11/2018 |
| WO | WO 2016/050887 A1 | 4/2016 |
| WO | 2018087688 A | 5/2018 |
| WO | WO 2018/087685 A1 | 5/2018 |

OTHER PUBLICATIONS

Smela, Thiol—Modified Pyrrole Monomers . . . ; Langmuir (1998) 14 pages 2970-2975. (Year: 1998).*
International Search Report form the European Patent Office in corresponding International Application No. PCT/IB2019/059473 mailed Nov. 5, 2019.
Written Opinion of the International Searching Authority from the European Patent Office in corresponding International Application No. PCT/IB2019/059473 mailed Nov. 5, 2019.
Notification of the First Office Action issued by the China National Intellectual Property Administration on Jan. 30, 2024, in corresponding Application No. CN 2019800096064.7 (6 pages).
Waddell, W. H., "Surface discoloring of black sidewall and relevant non-staining technology", China Academic Journal Electronic Publishing House, 1999, pp. 658-674.
Galimberti, M. et al., "Biobased Janus molecule for the facile preparation of water solutions of few layer graphene sheets", The Royal Society of Chemistry 2015, RSC Advances, 2015, 5, pp. 81142-81152.
Barbera, V. et al., "Facile and sustainable functionalization of graphene layers with pyrrole compounds", De Gruyter, Pure Application Chemistry 2018; 90(2): pp. 253-270.
Technical Specification, "Graphene and related two dimensional (2D) materials", ISO/TS 80004-13:2017(E), 11 pages.
Abdullateef, A. et al., "Natural Rubber Nanocomposites with Functionalized Carbon Nanotubes: Mechanical, Dynamic Mechanical, and Morphology Studies", Journal of Applied Polymer Science, vol. 125, E76-E84 (2012).
Galimberti, M. et al., "The Role of CNTs in Promoting Hybrid Filler Networking and Synergism with Carbon Black in the Mechanical Behavior of Filled Polyisoprene", Macromolecular Journals, Macromolecular Materials and Engineering, 2013, 298, pp. 241-251.

(Continued)

*Primary Examiner* — David J Buttner
(74) *Attorney, Agent, or Firm* — Finnegan, Henderson, Farabow, Garrett & Dunner, L.L.P.

(57) ABSTRACT

The present invention relates to adducts between $sp^2$ hybridized carbon allotropes and pyrrole derivatives comprising at least one sulphur atom, and crosslinkable elastomer compositions comprising such adducts. The present invention further relates to tyres for vehicle wheels comprising at least one structural element comprising a crosslinked elastomer material obtained by crosslinking of such crosslinkable elastomer compositions.

15 Claims, 9 Drawing Sheets

(56) References Cited

OTHER PUBLICATIONS

Figure 1:
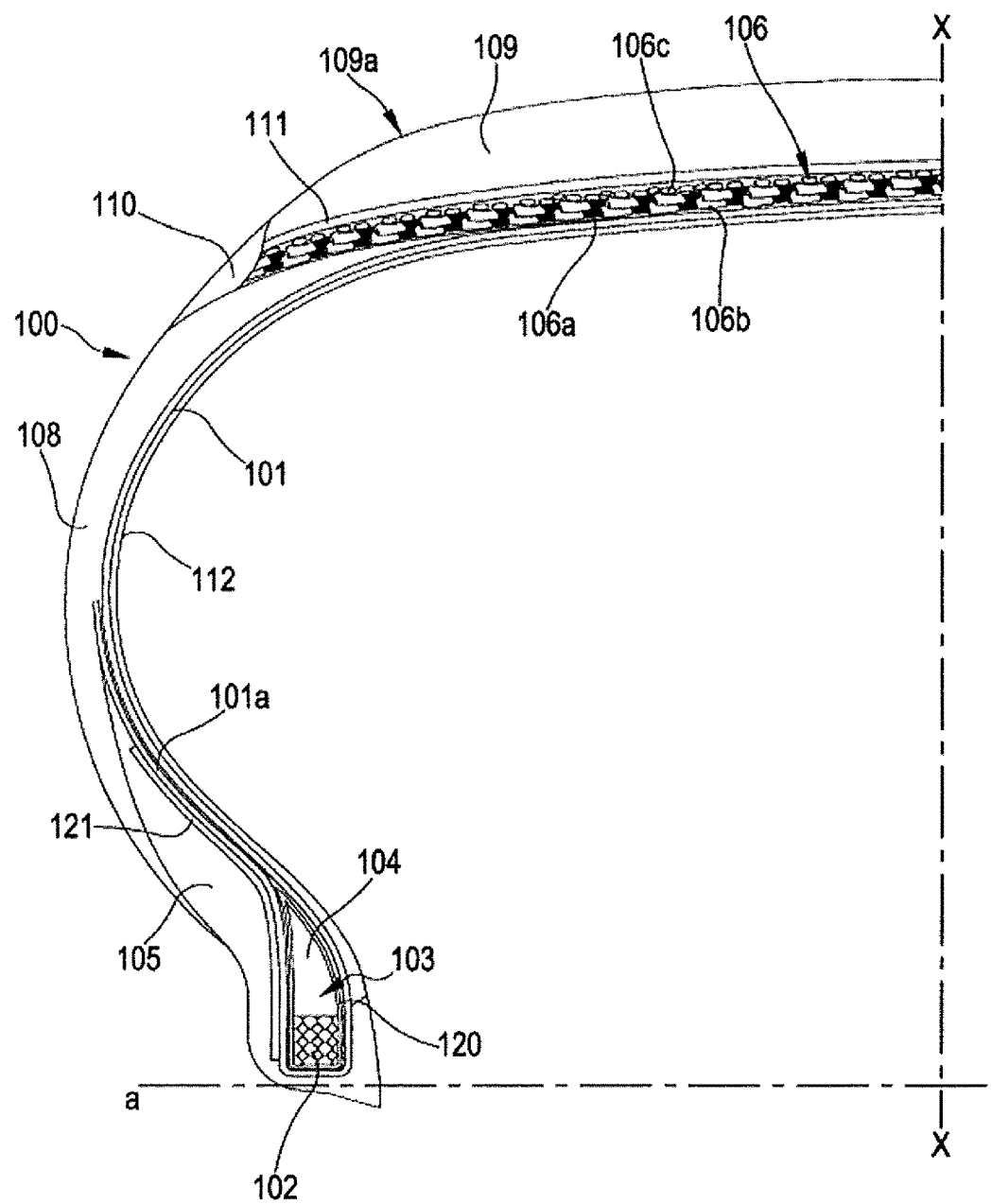

Galimberti, M. et al., "Facile Functionalization of sp² Carbon Allotropes With a Biobased *Janus* Molecule", Rubber Chemistry and Technology, vol. 90, No. 2, pp. 285-307 (2017).
Galimberti, M. et al., "Filler Networking of a Nanographite With a High Shape Anisotropy and Synergism With Carbon Black in Poly(1,4-CIS-Isoprene_-Based Nanocomposites", Rubber Chemistry and Technology, vol. 87, No. 2, pp. 197-218 (2014).
Barbera, V. et al., "Domino Reaction for the Sustainable Functionalization of Few-Layer Graphene", Nanomaterials 2019, 9, 44, 12 pages, www.mdpi.com/journal/nanomaterials.

\* cited by examiner

ADDUCTS BETWEEN CARBON ALLOTROPES AND PYRROLE DERIVATIVES, ELASTOMER MIXTURES COMPRISING THEM AND TYRES COMPRISING SUCH MIXTURES

This application is a national stage filing under 35 U.S.C. § 371 of International Application No. PCT/IB2019/059473, filed on Nov. 5, 2019, which claims priority to International Application No. PCT/EP2019/061707, filed on May 7, 2019; the contents of each application is incorporated herein by reference in their entirety.

FIELD OF THE INVENTION

The present invention relates to the development of novel adducts between pyrrole derivatives comprising at least one sulphur atom and carbon allotropes, as components for the production of crosslinked elastomer material for vehicle tyres and wheels.

PRIOR ART

Carbon black has been used for more than a century as a reinforcing filler for elastomers.

The reinforcing action of carbon black is due to its compatibility with the elastomer matrixes, to a large extent consisting of hydrocarbon polymers, and at the same time to its insolubility in the same; to its modulus, which is far greater than that of the elastomer matrix; to the sub-micrometre dimensions of its constituent particles and of the aggregates of these particles; and finally to its so-called "structure".

The term "structure" is used to indicate that these constituent particles are bound together via covalent bonds, leaving voids between them. These voids are capable of accommodating the polymer chains of an elastomer matrix, anchoring them and transforming them from a viscous fluid into a reinforcing filler. The greater the quantity of the empty spaces, the larger is the structure.

The sub-micrometre size of carbon black, and the consequent high surface area, furthermore allow good interaction and an extensive interface between the reinforcing filler and the polymer chains of an elastomer matrix, necessary prerequisites for the mechanical reinforcement.

Carbon black is a carbon allotrope with $sp^2$ hybridization. Other carbon allotropes with $sp^2$ hybridization are, for example, fullerene, carbon nanotubes, graphene and the nano-graphites with a few stacked layers of graphene. These allotropes have nanometre dimensions, and are, for the most part, endowed with a high aspect ratio, and hence a high surface area, and are therefore capable of establishing a high interfacial area with an elastomer matrix. They are thus potentially ideal fillers for giving major mechanical reinforcement to the elastomer matrixes.

Mechanical reinforcement is evaluated at both low and high deformation.

Reinforcement at low deformation depends mainly on the surface area of the reinforcing filler. A high surface area of the reinforcing filler promotes an extensive interaction with the polymer chains and with other particles of filler, essentially based on non-bonding forces. By applying energy and progressively increasing the deformation amplitude, the reinforcement based on non-bonding interactions ceases to exist and there is a reduction in the viscoelastic modulus, accompanied by dissipation of energy. This phenomenon is known as the Payne effect.

Conversely, the reinforcing action at high deformations is due to the stable interaction between the polymer matrix and the filler, which, in the case of traditional reinforcing fillers such as carbon black, is due to the structure of the filler, i.e. to the voids between the fundamental particles of the filler itself.

The main application of this type of elastomer compositions is in compounds for tyres, for which it is desirable to obtain a reinforcement which is constant with increasing deformation, i.e. to obtain a reduced Payne effect, with the aim of minimizing the dissipation of energy, which would otherwise cause greater fuel consumption and environmental impact.

The reduction in the Payne effect can be obtained by optimizing the dispersion of the reinforcing filler, for example carbon black, in the elastomer matrix, separating the aggregates and/or the elemental particles from it, covering them with a layer of elastomer. Various possibilities for obtaining this optimization are known in the art, such as for example: (i) mixing the allotrope with the elastomer matrix by means of mechanical energy, (ii) dissolution of the elastomer matrix in solvent and subsequent mixing (iii) chemical modification of the allotrope with the aim of obtaining a solubility parameter as similar as possible to that of the matrix or with the aim of rendering the allotrope itself dispersible in an aqueous latex of the elastomer which constitutes the matrix.

The use of mechanical energy is the modality currently most used at the industrial level. However, this presents some disadvantages: the high energy of mixing leads to degradation of the polymer matrix and/or the reinforcing filler (see for example Macromol. Mater. Eng. 2012, 298, 241-251), and the thermodynamic incompatibility of the carbon allotrope with the elastomer leads in time to re-agglomeration of the filler (see for example Rubber Chemistry and Technology 2014, 87, 2, 197-218).

On the other hand, as regards the possibility of obtaining a mixture in solvent, the first attempts reported in the art generally make use of aromatic solvents, such as for example toluene (see for example Journal of Applied Polymer Science 2012, 125, E76-E84). This, together with the complexity of the procedure, renders the possibility of industrial development difficult.

In recent years, research has therefore been focused on the chemical modification of the reinforcing fillers, for example carbon black, with the aim of increasing its compatibility with elastomer matrixes.

Matos et al. (Carbon 2012, 50, 4685-4695) reported the preparation of composite materials comprising natural rubber and nanotubes of carbon comprising magnetic species in their cavities and treated with sodium dodecyl sulphate (SDS). The procedure for creating the adduct is complex and the adduct is compatible only with polymer latex.

Further, although the carbon allotrope may have been rendered more compatible with the polymer, it is nonetheless not capable of forming any chemical bond with it.

EP3209604B1 and WO2018/087685A1, in the Applicants' name, describe adducts between $sp^2$ hybridized carbon allotropes and pyrrole derivatives capable of modifying the compatibility of the carbon allotropes towards a vast range of solid and liquid matrixes. The inventors further described the preparation of stable dispersions of such adducts in water (see also RSC Adv., 2015, 5(99), 81142-81152) and in latexes of natural rubber (see also Rubber Chem. Technol., 2017, 90(2), 285-307).

Other attempts at modifying the chemical and physical properties of reinforcing fillers with the aim of increasing their compatibility with elastomer matrixes have been described in the art.

US 2015/0191579 A1 describes agglomerates of carbon black on the surface of which inorganic polysulphides are adsorbed, the elastomer compositions which contain them and tyres containing such elastomer compositions.

The reduction in the Payne effect, with consequent reduction in the dissipation of energy, is one of the primary objectives in tyre production, in particular for tread compounds, which represent the major component of the tyre itself in quantitative and qualitative terms.

SUMMARY OF THE INVENTION

The Applicant addressed the need to obtain elastomer compositions comprising commercially available elastomers and $sp^2$ hybridized carbon allotropes, characterized by optimal dispersion and by a stable interaction between the carbon allotrope and the polymer chains of the elastomer matrix, and in which the carbon allotropes maintain their $sp^2$ nature substantially unchanged.

The Applicant has also addressed the need to obtain such elastomer compositions by means of simple techniques, with reduced environmental impact, and using the standard solid state mixing techniques used in the tyres industry.

Surprisingly, the Applicant has found that adducts between $sp^2$ hybridized carbon allotropes and pyrrole derivatives comprising one or more sulphur atoms can be dispersed more efficiently than expected in elastomer matrixes, forming a stable interaction with these. The elastomer compositions thus obtained exhibit low hysteresis and a reduced Payne effect, with consequent reduced dissipation of energy, and are thus particularly suitable as compounds for tyres, in particular for the tread band.

The invention thus relates to an adduct between an $sp^2$ hybridized carbon allotrope and a pyrrole derivative, wherein the pyrrole derivative is represented by formula (1)

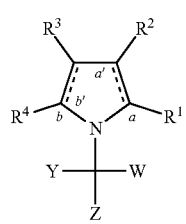

(1)

wherein $R_1$, $R_2$, $R_3$, and $R_4$ are independently selected in the group consisting of: hydrogen, linear or branched $C_1$-$C_{22}$ alkyl, linear or branched $C_2$-$C_{22}$ alkenyl or alkynyl, aryl, linear or branched $C_1$-$C_{22}$ alkyl-aryl, linear or branched $C_2$-$C_{22}$ alkenyl-aryl, linear or branched $C_2$-$C_{22}$ alkynyl-aryl, and heteroaryl;

the dashed lines (a') and (b') independently represent a double bond or a single bond; and W, Y and Z are independently selected from the group consisting of: hydrogen, linear or branched $C_1$-$C_{18}$ alkyl, linear or branched $C_2$-$C_{18}$ alkenyl or alkynyl, and the below indicated formulae (II)-(V)

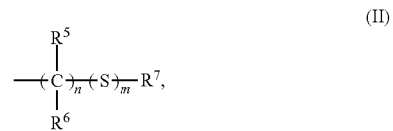

(II)

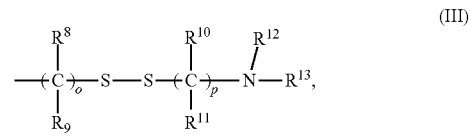

(III)

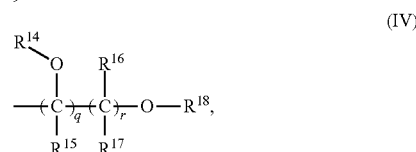

(IV)

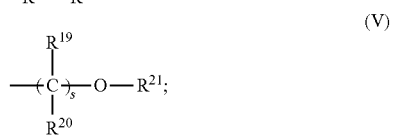

(V)

wherein $R_5$, $R_6$, $R_7$, $R_8$, $R_9$, $R_{10}$, $R_{11}$, $R_{12}$, $R_{13}$, $R_{14}$, $R_{15}$, $R_{16}$, $R_{17}$, $R_{18}$, $R_{19}$, $R_{20}$, and $R_{21}$ are independently selected from the group consisting of: hydrogen, linear or branched $C_1$-$C_{18}$ alkyl, linear or branched $C_2$-$C_{18}$ alkenyl or alkynyl, aryl, linear or branched $C_1$-$C_{22}$ alkyl-aryl, linear or branched $C_2$-$C_{22}$ alkenyl-aryl, linear or branched $C_2$-$C_{22}$ alkynyl-aryl, heteroaryl, carboxyl, acyl-alkyl with linear or branched $C_1$-$C_{18}$ alkyl, acyl-alkenyl or acyl-alkynyl with linear or branched $C_2$-$C_{18}$ alkenyl and alkynyl, acyl-aryl, acyl-heteroaryl, and acyl-amine, wherein said aryl and heteroaryl groups are optionally substituted by one or more groups selected from $C_1$-$C_3$ alkyl, carboxyl, and acyl-alkyl with $C_1$-$C_3$ alkyl;

or $R_{12}$ and $R_{13}$ together form a pyrrole ring optionally substituted by one or more $C_1$-$C_3$ alkyl groups;

and wherein m is an integer from 1 to 4, and n, o, p, q, r, and s are, independently of one another, an integer from 1 to 12;

and wherein when both the dashed lines (a') and (b') represent a double bond, then formula (1) is represented by formula (1a) wherein $R_1$-$R_4$ and W, Y, and Z have the meanings stated above,

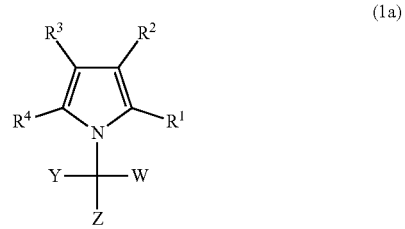

(1a)

and on condition that at least one among W, Y, and Z is represented by one of the formulae (II)-(III) above, or when only the dashed line (b') represents a double bond, then Y is hydrogen, W is a —$CH_2$—S— group which together with the carbon in position "a" forms a 5-membered ring, and formula (1) is represented by formula (1b) wherein $R_1$-$R_4$ and Z have the meanings stated above

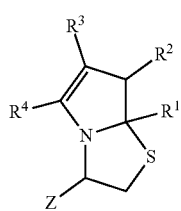

(Ib)

or, when both the dashed lines represent a single bond, then Y and W are both a —CH$_2$—S— group, and each of them together with the carbons in position "a" and "b" forms a 5-membered ring, and formula (1) is represented by formula (1c) wherein R$_1$-R$_4$ and Z have the meanings stated above

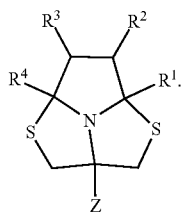

(Ic)

A second aspect of the present invention relates to a process for obtaining the adducts between sp$^2$ hybridized carbon allotropes and pyrrole derivatives comprising at least one sulphur atom as described above, wherein such process comprises the steps of:
 a) forming a mixture of at least one compound of formula (1) as described above and of at least one sp$^2$ hybridized carbon allotrope; and
 b) supplying energy to the mixture obtained to effect an interaction between functional groups of the compound of formula (1) and said allotrope.

A third aspect of the present invention is represented by the use of the adducts between sp$^2$ hybridized carbon allotropes and pyrrole derivatives comprising at least one sulphur atom as described above for the preparation of compositions, preferably elastomer compositions.

A fourth aspect of the present invention is represented by a crosslinkable elastomer composition comprising the adducts between sp$^2$ hybridized carbon allotropes and pyrrole derivatives comprising at least one sulphur atom according to the present invention.

A fifth and last aspect of the present invention is represented by a tyre for vehicle wheels comprising at least one structural element comprising a crosslinked elastomer material obtained by crosslinking of a crosslinkable elastomer composition according to the present invention.

BRIEF DESCRIPTION OF THE DIAGRAMS

The description is illustrated here with reference to the attached drawings, provided solely by way of example and not limiting the invention.

FIG. 1: outline of the transverse half-section of an automobile tyre comprising in one or more components the elastomer composition according to the present invention.

Figure 2:
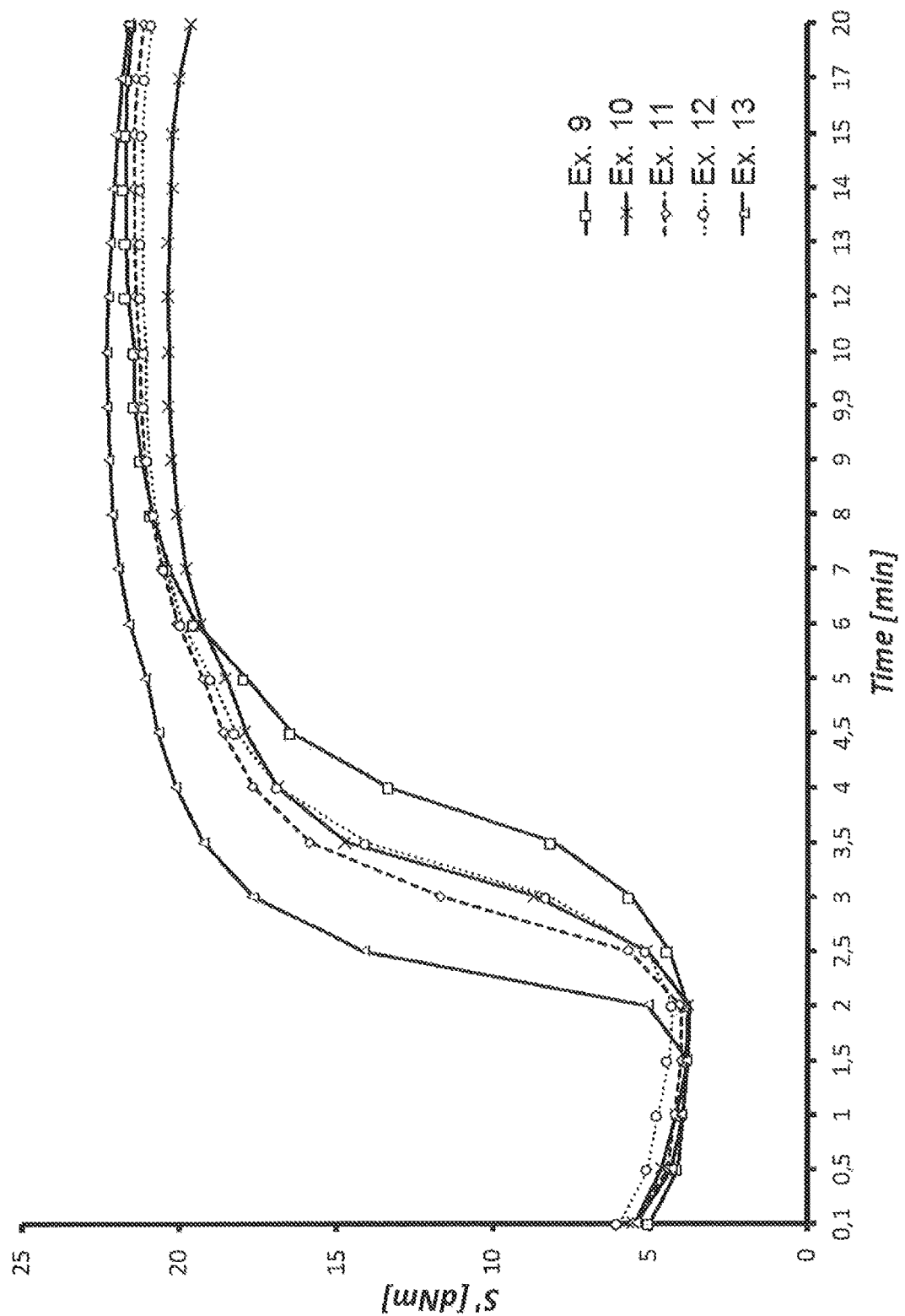

FIG. 2: is a graph showing the vulcanization curves of the elastomer compositions of examples 9-13, where the time (mins) is shown on the x axis and the torque needed to effect the rotation of the rheometer disk in the material which is in the vulcanization stage, is shown on the y axis. This torque is indicated as S' and the measurement unit is dNm.

Figure 3:
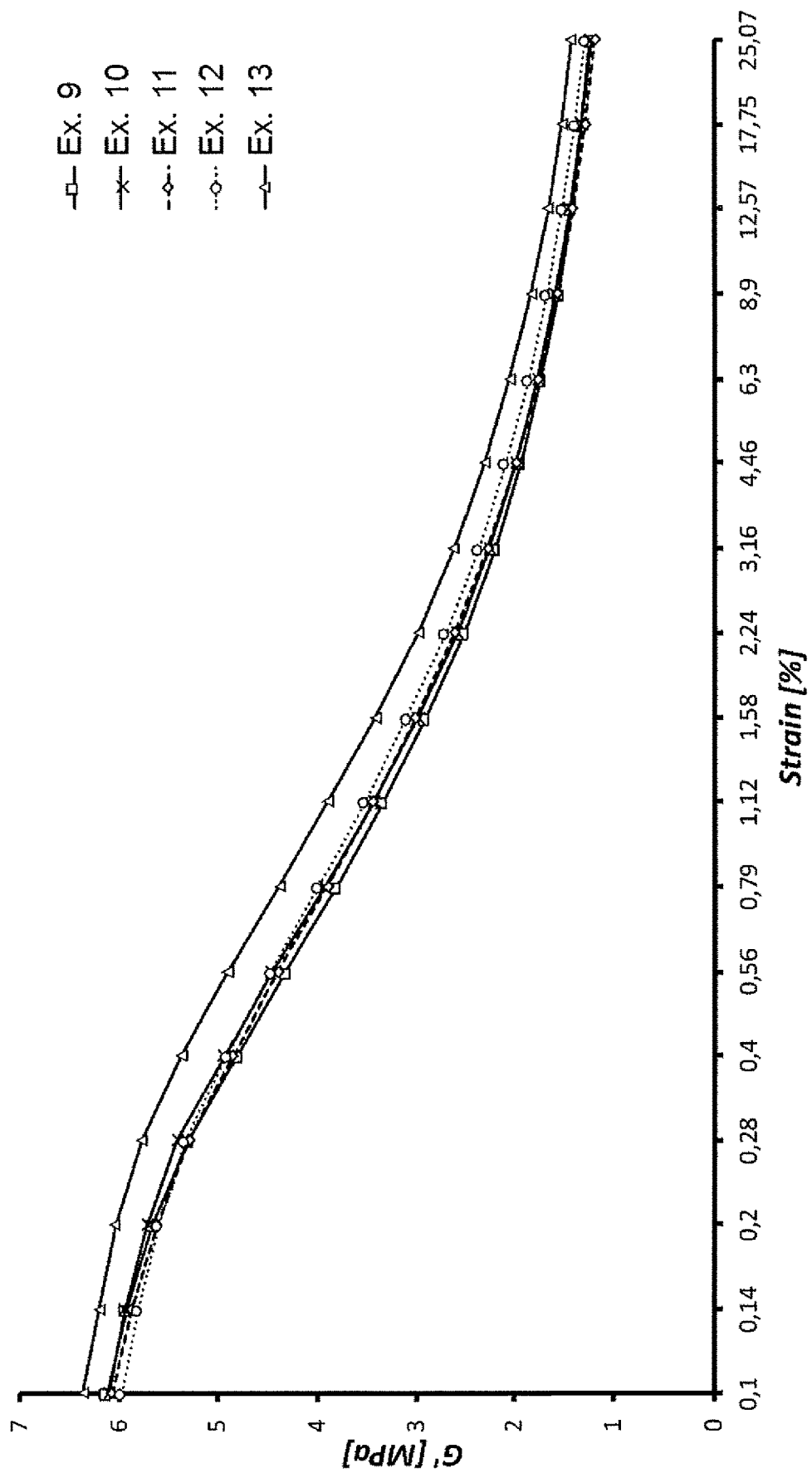
Figure 4:
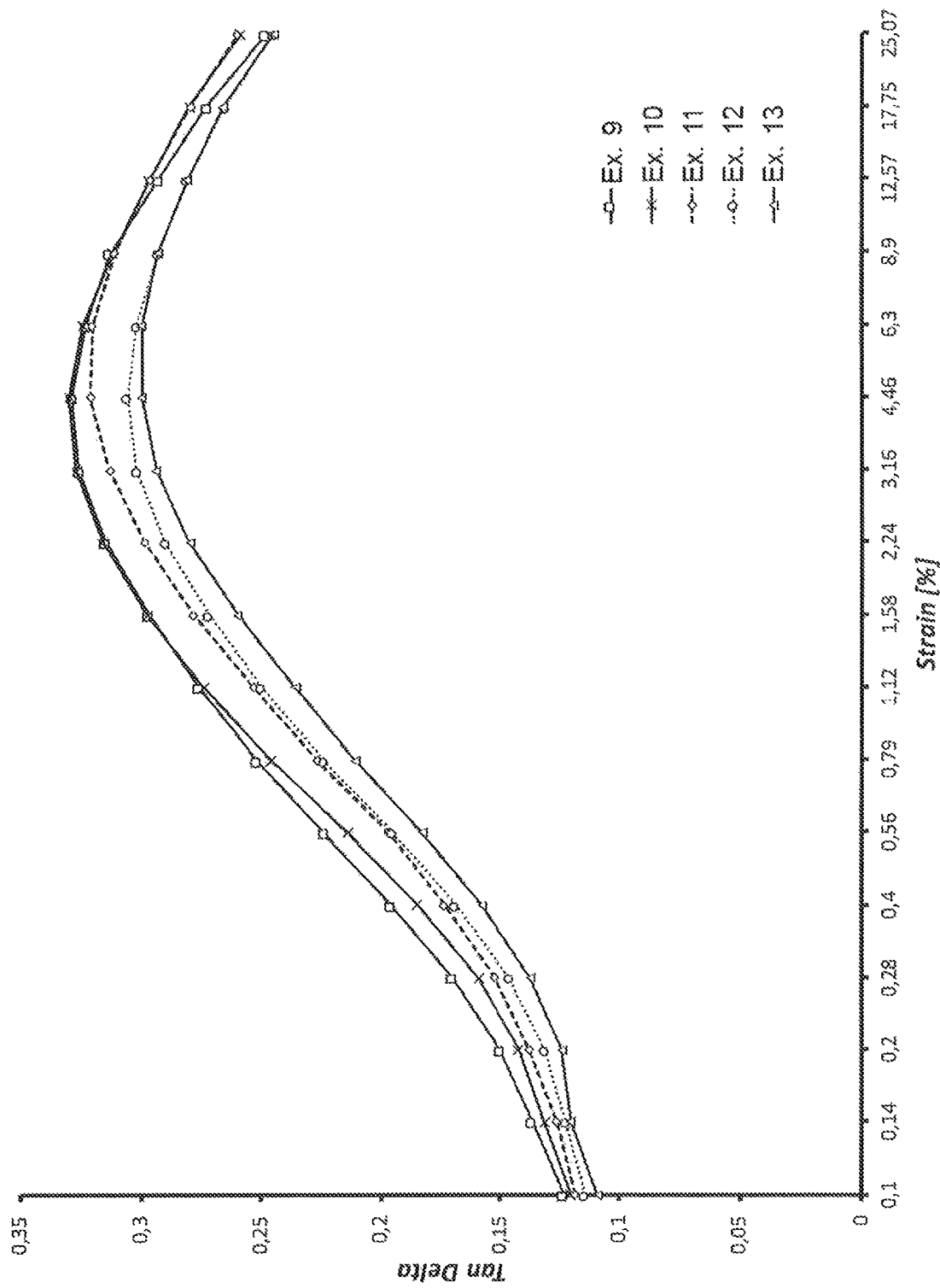
Figure 5:
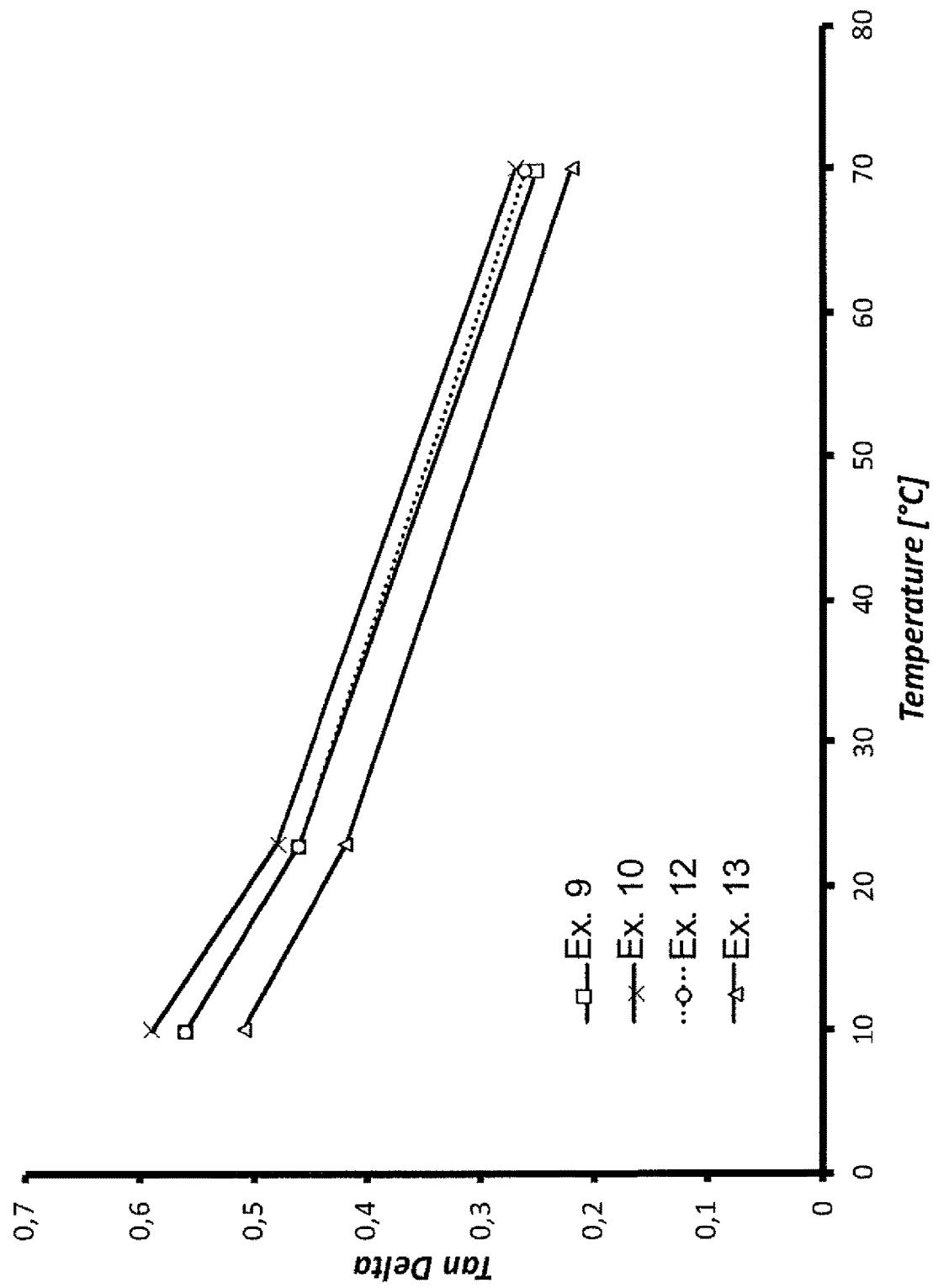
Figure 6:
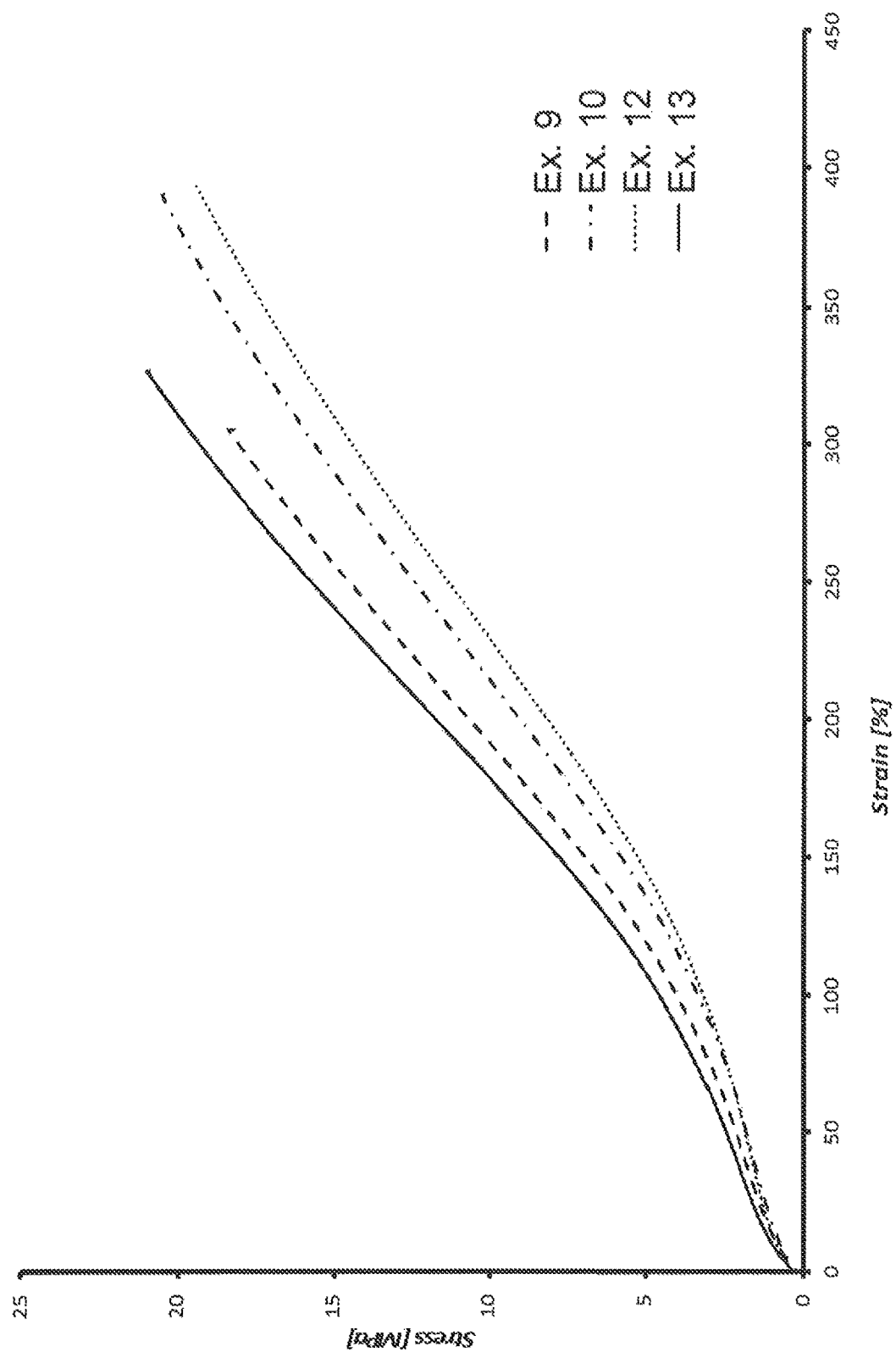
Figure 7:
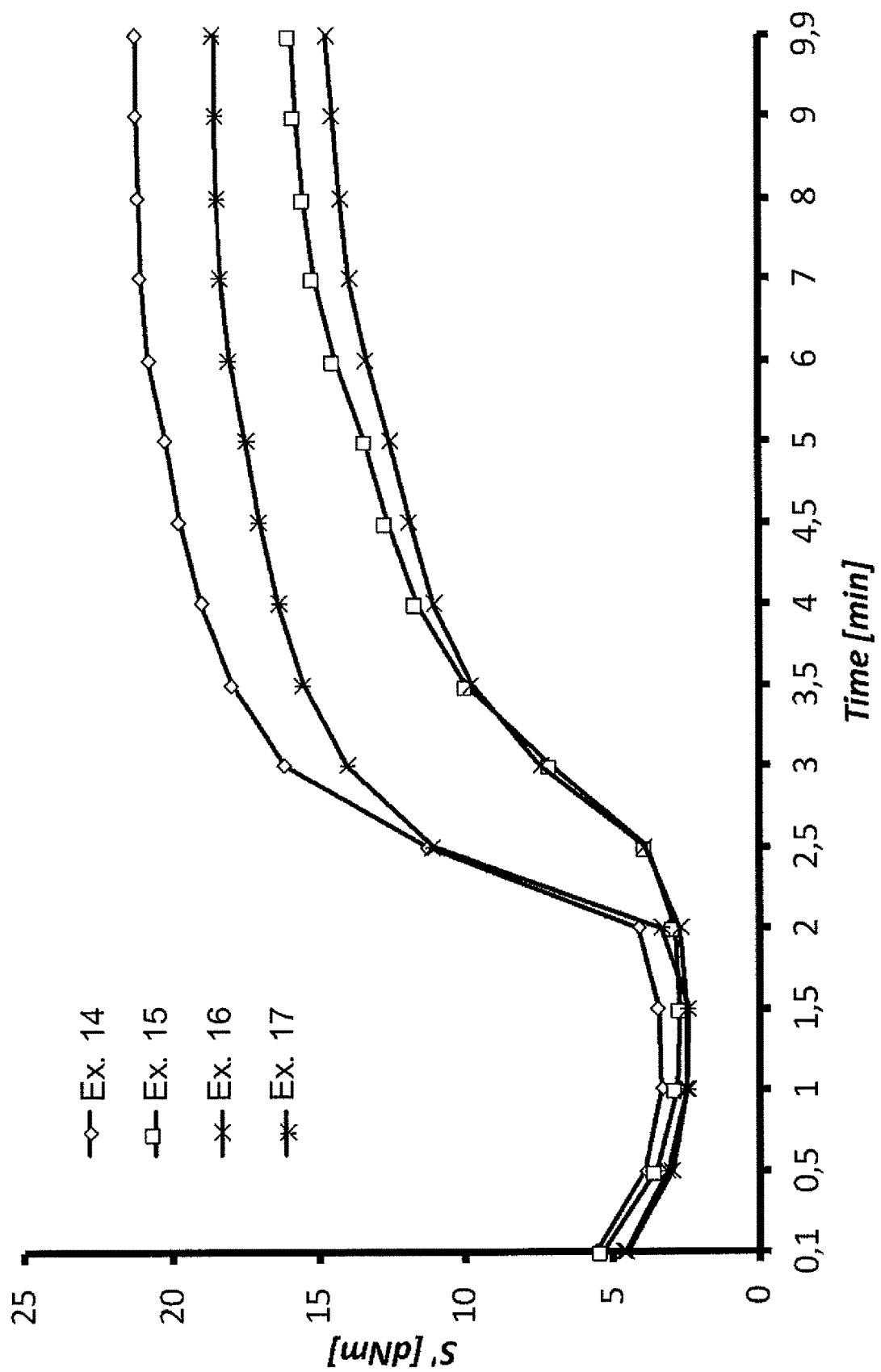

FIG. 3: is a graph showing the variation of G' (y axis) versus the deformation amplitude (x axis) for the elastomer compositions of examples 9-13;

FIG. 4: is a graph showing the variation of tan delta (y axis) versus the deformation amplitude (x axis) for the elastomer compositions of examples 9-13;

FIG. 5: is a graph showing the dependence of the values of tan delta (y axis) on the temperature (x axis) for the elastomer compositions of examples 9-10 and 12-13;

FIG. 6: is a graph showing the variation of the stress (y axis) versus the strain (x axis) for the elastomer compositions of examples 9-10 and 12-13;

FIG. 7: is a graph showing the vulcanization curves of the elastomer compositions of examples 14-17, where the time (mins) is shown on the x axis and the torque necessary to effect the rotation of the rheometer disk in the material which is in the vulcanization step is shown on the y axis. This torque is indicated as S' and the measurement unit is dNm.

Figure 8:
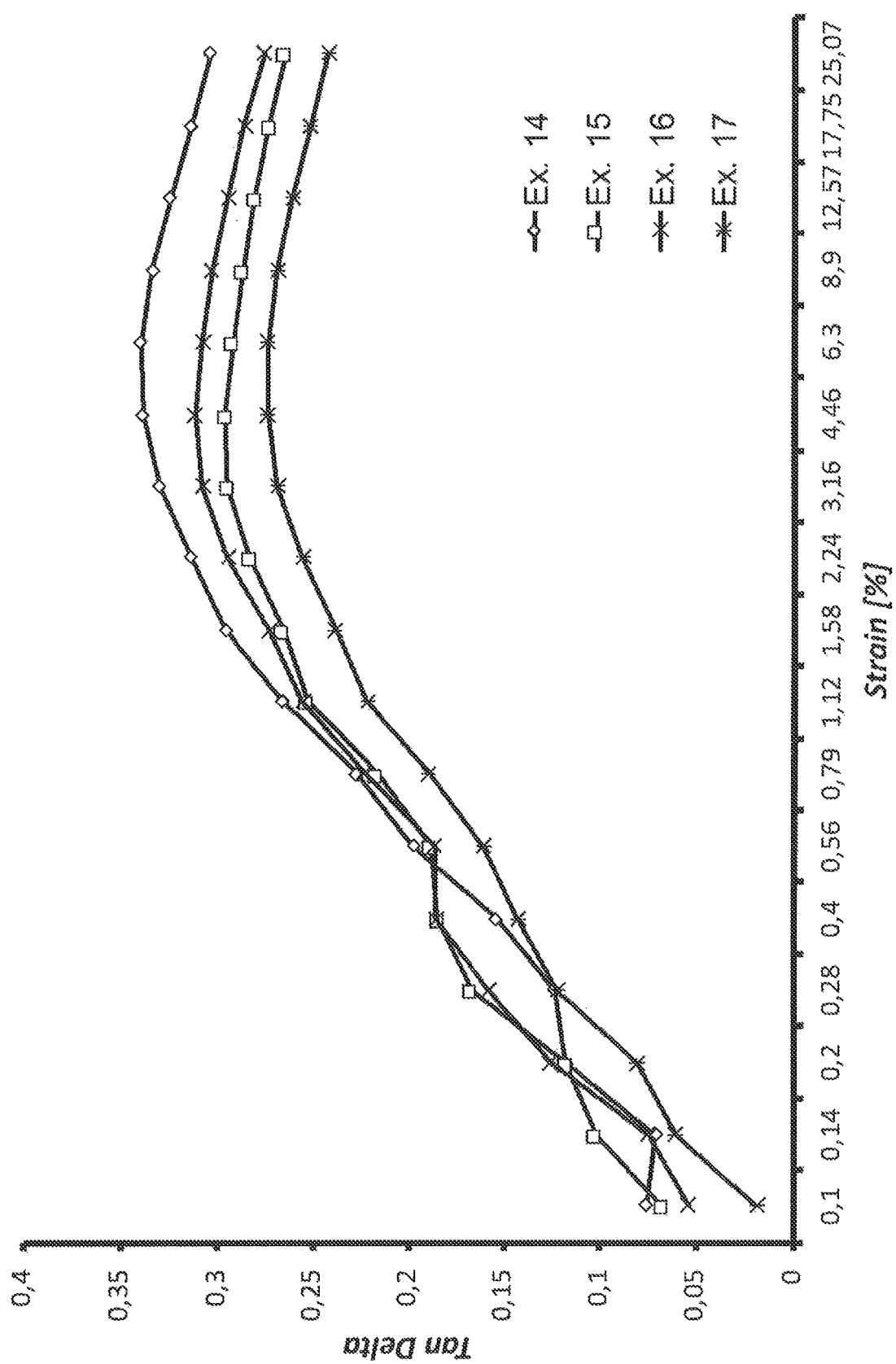
Figure 9:
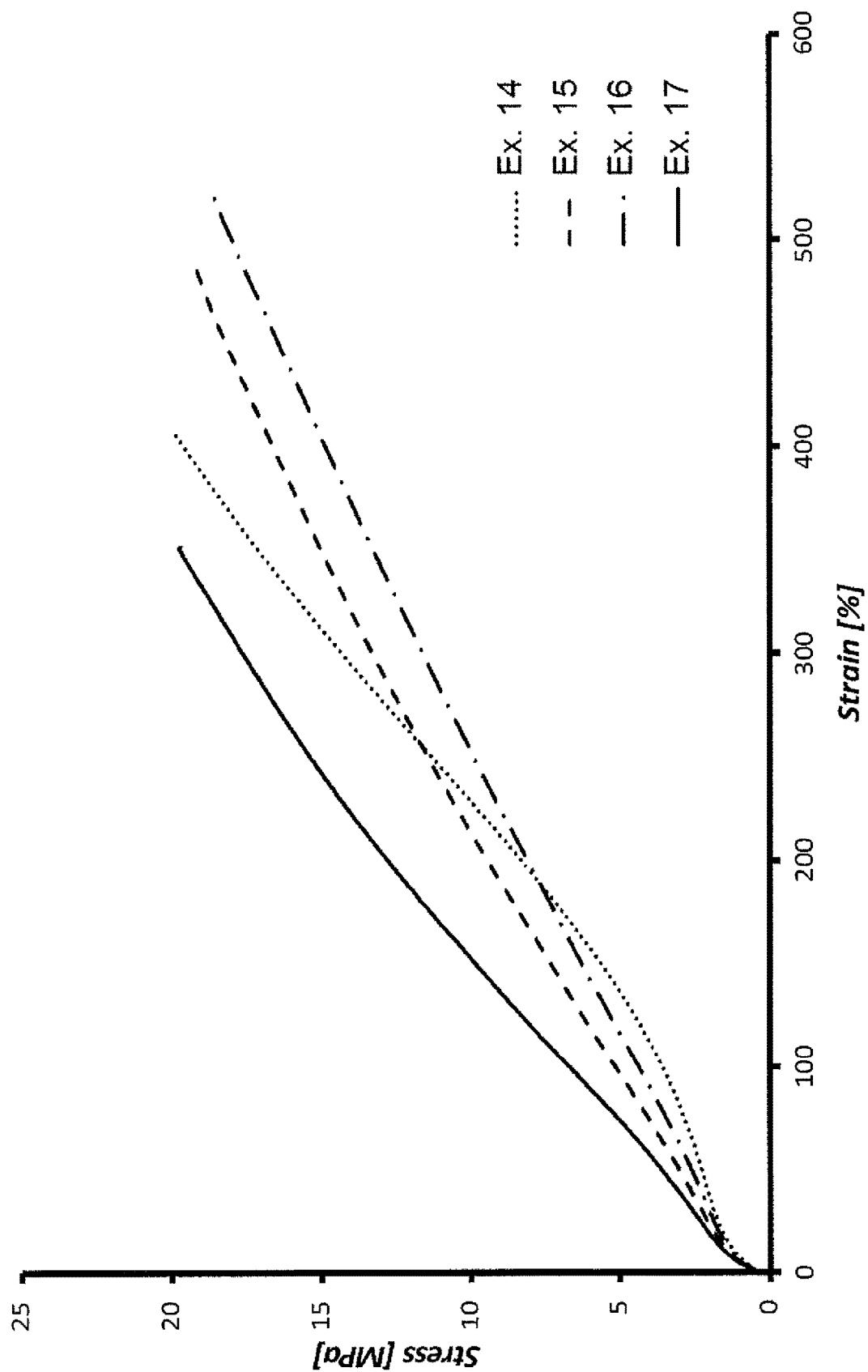

FIG. 8: is a graph showing the variation of Tan delta (y axis) versus the deformation amplitude (x axis) for the elastomer compositions of examples 14-17; and FIG. 9: is a graph showing the variation of the stress (y axis) versus the strain (x axis) for the elastomer compositions of examples 14-17.

DETAILED DESCRIPTION OF THE INVENTION

Definitions

In the present description, the term "pyrrole derivative(s)" is understood to mean a compound of formula (1) as defined above and in the appended claims. In the invention, the pyrrole derivative of formula 1 is also defined as a pyrrole derivative comprising at least one sulphur atom.

According to the present invention, the term "adduct" is understood to mean a compound obtained via an addition reaction; more specifically, the term adduct indicates those particular addition compounds whose components bound more or less loosely, i.e. via covalent bonds or by means of more labile intermolecular interactions, retain their individuality in some ways. In particular according to the present invention, the term "adduct(s)" is used to refer to an adduct obtained from the interaction, via covalent or noncovalent bonds, between a pyrrole derivative comprising at least one sulphur atom and an sp$^2$ hybridized carbon allotrope.

According to the present description, the terms "carbon allotrope" and "carbon-based filler" are used interchangeably, and/or are both indicated with the abbreviation CA.

For the purposes of the present description and the following claims, the term "phr" (parts per hundreds of rubber) indicates the parts by weight of a defined component of the elastomer composition per 100 parts by weight of the elastomer polymer.

The term "graphene" is used to refer generally to a structure comprising one or at the most a few layers of carbon atoms organized in hexagonal aromatic rings. According to the guidelines established by the International Organization for Standardization (ISO) the terms "bi-layer graphene" and "few layer graphene" respectively indicate a graphene with 2 layers and a graphene with from 3 to 10 layers of carbon atoms organized in hexagonal aromatic rings, according to the definition established by the ISO (Organization for Standardization (ISO) Nanotechnologies—Vocabulary—Part 13: Graphene and Related Two-Dimensional (2D) Materials, BSI Standards Publication, London, UK 2017). According to such guidelines, beyond the 10 layers, the resulting material typically assumes the characteristics (in particular the electrical characteristics) of graphite.

DETAILED DESCRIPTION

A first aspect of the present invention is an adduct between an $sp^2$ hybridized carbon allotrope and a pyrrole derivative, wherein the pyrrole derivative is represented by formula (1)

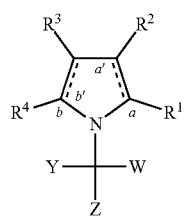

(1)

wherein $R_1$, $R_2$, $R_3$, and $R_4$ are independently selected in the group consisting of: hydrogen, linear or branched $C_1$-$C_{22}$ alkyl, linear or branched $C_2$-$C_{22}$ alkenyl or alkynyl, aryl, linear or branched $C_1$-$C_{22}$ alkyl-aryl, linear or branched $C_2$-$C_{22}$ alkenyl-aryl, linear or branched $C_2$-$C_{22}$ alkynyl-aryl, and heteroaryl;

the dashed lines (a') and (b') independently represent a double bond or a single bond; and W, Y and Z are independently selected from the group consisting of: hydrogen, linear or branched $C_1$-$C_{18}$ alkyl, linear or branched $C_2$-$C_{18}$ alkenyl or alkynyl, and the below identified formulae (II)-(V)

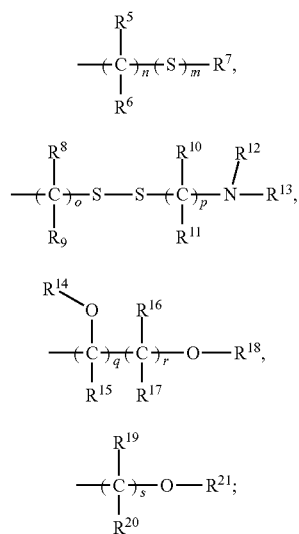

wherein $R_5$, $R_6$, $R_7$, $R_8$, $R_9$, $R_{10}$, $R_{11}$, $R_{12}$, $R_{13}$, $R_{14}$, $R_{15}$, $R_{16}$, $R_{17}$, $R_{18}$, $R_{19}$, $R_{20}$, and $R_{21}$ are independently selected from the group consisting of: hydrogen, linear or branched $C_1$-$C_{18}$ alkyl, linear or branched $C_2$-$C_{18}$ alkenyl or alkynyl, aryl, linear or branched $C_1$-$C_{22}$ alkyl-aryl, linear or branched $C_2$-$C_{22}$ alkenyl-aryl, linear or branched $C_2$-$C_{22}$ alkynyl-aryl, heteroaryl, carboxyl, acyl-alkyl with linear or branched $C_1$-$C_{18}$ alkyl, acyl-alkenyl or acyl-alkynyl with linear or branched $C_2$-$C_{18}$ alkenyl and alkynyl, acyl-aryl, acyl-heteroaryl, and acyl-amine, wherein said aryl and heteroaryl groups are optionally substituted by one or more groups selected from $C_1$-$C_3$ alkyl, carboxyl, and acyl-alkyl with $C_1$-$C_3$ alkyl;

or $R_{12}$ and $R_{13}$ together form a pyrrole ring optionally substituted by one or more $C_1$-$C_3$ alkyl groups;

and wherein m is an integer from 1 to 4, and n, o, p, q, r, and s are, independently of one another, an integer from 1 to 12;

and wherein when both the dashed lines (a') and (b') represent a double bond, then formula (1) is represented by formula (1a) wherein $R_1$-$R_4$ and W, Y, and Z have the meanings stated above,

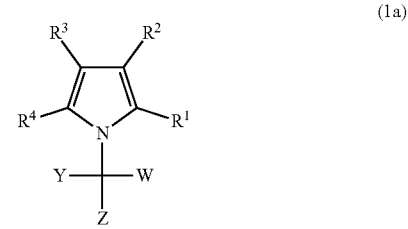

(1a)

and on condition that at least one among W, Y, and Z is represented by one of the formulae (II)-(III) above;

or when only the dashed line (b') represents a double bond, then Y is hydrogen, W is a —$CH_2$—S— group which together with the carbon in position "a" forms a 5-membered ring, and formula (1) is represented by formula (1 b) wherein $R_1$-$R_4$ and Z have the meanings stated above

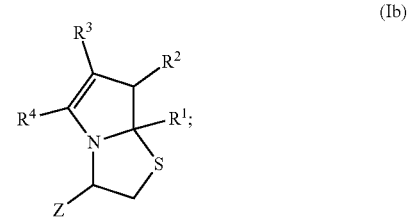

(1b)

or, when both the dashed lines represent a single bond, then Y and W are both a —$CH_2$—S— group, and each of them together with the carbons in position "a" and "b" forms a 5-membered ring, and formula (1) is represented by formula (1c) wherein $R_1$-$R_4$ and Z have the meanings stated above

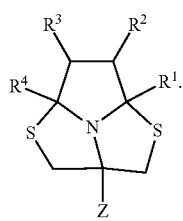

(1c)

By convention, in formula 1b the dashed line (b') in formula (1) is indicated to represent a double bond, contemplating also the possibility that the dashed line (a') in formula (1) may represent a double bond.

Preferably the sp² hybridized carbon allotropes used to prepare the adducts according to the present invention are selected in the group consisting of carbon black, graphene (possibly graphene with 2 layers (bi-layer graphene) or graphene with few layers (from 3 to 10; few layer graphene)), graphite, in particular high surface area graphite, single wall or multiwall carbon nanotubes, carbon nanotubes with longitudinal or helicoid extension, nanocones, nanohorns, nanotoroids, other structures of nanotubes or graphene structures (for example clusters of graphene, ribbons of graphene, 2D or 3D networks of graphene or nanotubes, crystals of graphite), fullerene.

More preferably, the sp² hybridized carbon allotropes are selected in the group comprising carbon black, fullerene, single wall or multiwall carbon nanotubes with 2 layers (bi-layer graphene), graphene with few layers (from 3 to 10; few layer graphene), graphite, in particular high surface area graphite, or mixtures thereof.

Still more preferably, the sp² hybridized carbon allotropes are selected in the group consisting of carbon black, graphene with 2 layers (bi-layer graphene), graphene with few layers (from 3 to 10; few layer graphene), graphite (for example with a number of graphene layers lying between 10 and 10,000), in particular high surface area graphite, single wall or multiwall carbon nanotubes or mixtures thereof.

In a particularly preferred embodiment, the sp² hybridized carbon allotrope is carbon black alone or mixed with one or more carbon allotropes.

In another particularly preferred embodiment, the sp² hybridized carbon allotrope is high surface area graphite alone or mixed with other carbon allotropes.

In one embodiment the sp² hybridized carbon allotrope contains functional groups selected in the group comprising:
oxygenated groups, preferably hydroxyls or epoxides;
groups containing carbonyls, preferably aldehydes, ketones or carboxylic acids;
groups containing nitrogen atoms, preferably amines, amides, nitriles, diazonium salts or imines;
groups containing sulphur atoms, preferably sulphides, disulphides, mercaptans, sulfones, or sulfiinic and sulphonic groups.

According to one embodiment of the present invention, the pyrrole derivatives used to prepare the adducts are represented by formula (1a)

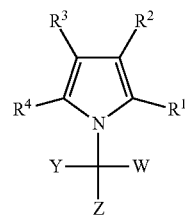

(1a)

wherein
$R_1, R_2, R_3$, and $R_4$ are independently selected in the group consisting of: hydrogen, linear or branched $C_1$-$C_{22}$ alkyl, linear or branched $C_2$-$C_{22}$ alkenyl or alkynyl, aryl, linear or branched $C_1$-$C_{22}$ alkyl-aryl, linear or branched $C_2$-$C_{22}$ alkenyl-aryl, linear or branched $C_2$-$C_{22}$ alkynyl-aryl, and heteroaryl;
W, Y and Z are independently selected from the group consisting of: hydrogen, linear or branched $C_1$-$C_{18}$ alkyl, linear or branched $C_2$-$C_{18}$ alkenyl or alkynyl, and the below formulae (II)-(V)

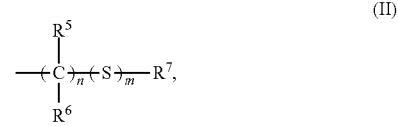

(II)

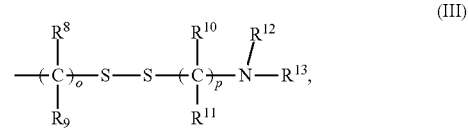

(III)

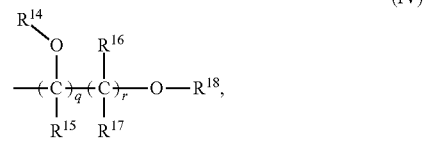

(IV)

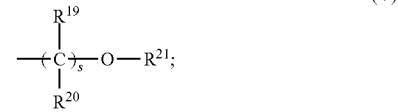

(V)

wherein $R_5, R_6, R_7, R_8, R_9, R_{10}, R_{11}, R_{12}, R_{13}, R_{14}, R_{15}, R_{16}, R_{17}, R_{18}, R_{19}, R_{20}$, and $R_{21}$ are independently selected from the group consisting of: hydrogen, linear or branched $C_1$-$C_{18}$ alkyl, linear or branched $C_2$-$C_{18}$ alkenyl or alkynyl, aryl, linear or branched $C_1$-$C_{22}$ alkyl-aryl, linear or branched $C_2$-$C_{22}$ alkenyl-aryl, linear or branched $C_2$-$C_{22}$ alkynyl-aryl, heteroaryl, carboxyl, acyl-alkyl with linear or branched $C_1$-$C_{18}$ alkyl, acyl-alkenyl or acyl-alkynyl with linear or branched $C_2$-$C_{18}$ alkenyl and alkynyl, acyl-aryl, acyl-heteroaryl, and acyl-amine, wherein said aryl and heteroaryl groups are optionally substituted by one or more groups selected from $C_1$-$C_3$ alkyl, carboxyl, and acyl-alkyl with $C_1$-$C_3$ alkyl;
or $R_{12}$ and $R_{13}$ together form a pyrrole ring optionally substituted by one or more $C_1$-$C_3$ alkyl groups;

and wherein m is an integer from 1 to 4, and n, o, p, q, r, and s are, independently from one another, an integer from 1 to 12;

on condition that at least one among W, Y, and Z is represented by one of the formulae (II)-(III) above.

Preferably, according to this embodiment, the pyrrole derivatives used to prepare the adducts are represented by formula (1a)

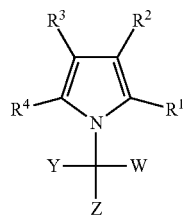
(1a)

wherein $R_1$, $R_2$, $R_3$, and $R_4$ are independently selected in the group consisting of: hydrogen, linear or branched $C_1$-$C_{22}$ alkyl, linear or branched $C_2$-$C_{22}$ alkenyl or alkynyl, aryl, linear or branched $C_1$-$C_{22}$ alkyl-aryl, linear or branched $C_2$-$C_{22}$ alkenyl-aryl, linear or branched $C_2$-$C_{22}$ alkynyl-aryl, and heteroaryl;

W is selected from the group consisting of: hydrogen, linear or branched $C_1$-$C_{18}$ alkyl and linear or branched $C_2$-$C_{18}$ alkenyl or alkynyl; and Y and Z are independently represented by one of the formulae (II)-(III) below

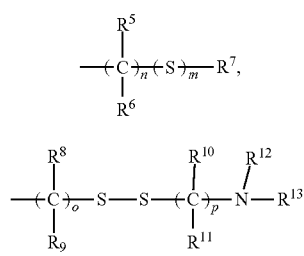

wherein $R_5$, $R_6$, $R_7$, $R_8$, $R_9$, $R_{10}$, $R_{11}$, $R_{12}$, and $R_{13}$ are independently selected from the group consisting of: hydrogen, linear or branched $C_1$-$C_{18}$ alkyl, linear or branched $C_2$-$C_{18}$ alkenyl or alkynyl, aryl, linear or branched $C_1$-$C_{22}$ alkyl-aryl, linear or branched $C_2$-$C_{22}$ alkenyl-aryl, linear or branched $C_2$-$C_{22}$ alkynyl-aryl, heteroaryl, carboxyl, acyl-alkyl with linear or branched $C_1$-$C_{18}$ alkyl, acyl-alkenyl or acyl-alkynyl with linear or branched $C_2$-$C_{18}$ alkenyl and alkynyl, acyl-aryl, acyl-heteroaryl, and acyl-amine, wherein said aryl and heteroaryl groups are optionally substituted by one or more groups selected from $C_1$-$C_3$ alkyl carboxyl, and acyl-alkyl with $C_1$-$C_3$ alkyl;

or $R_{12}$ and $R_{13}$ together form a pyrrole ring optionally substituted by one or more $C_1$-$C_3$ alkyl groups;

and wherein m is an integer from 1 to 4, and n, o, p are, independently of one another, an integer from 1 to 12.

Alternatively, the pyrrole derivatives used to prepare the adducts are represented by formula (1a)

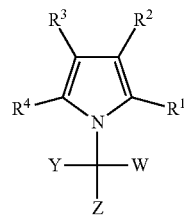
(1a)

wherein $R_1$, $R_2$, $R_3$, and $R_4$ are independently selected in the group consisting of: hydrogen, linear or branched $C_1$-$C_{22}$ alkyl, linear or branched $C_2$-$C_{22}$ alkenyl or alkynyl, aryl, linear or branched $C_1$-$C_{22}$ alkyl-aryl, linear or branched $C_2$-$C_{22}$ alkenyl-aryl, linear or branched $C_2$-$C_{22}$ alkynyl-aryl, and heteroaryl;

W and Y are independently selected from the group consisting of: hydrogen, linear or branched $C_1$-$C_{18}$ alkyl, linear or branched $C_2$-$C_{18}$ alkenyl or alkynyl; and Z is represented by one of the formulae (II)-(III) below

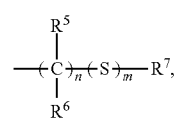
(II)

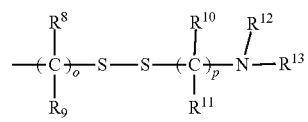
(III)

wherein $R_5$, $R_6$, $R_7$, $R_8$, $R_9$, $R_{10}$, $R_{11}$, $R_{12}$, and $R_{13}$ are independently selected from the group consisting of: hydrogen, linear or branched $C_1$-$C_{18}$ alkyl, linear or branched $C_2$-$C_{18}$ alkenyl or alkynyl, aryl, linear or branched $C_1$-$C_{22}$ alkyl-aryl, linear or branched $C_2$-$C_{22}$ alkenyl-aryl, linear or branched $C_2$-$C_{22}$ alkynyl-aryl, heteroaryl, carboxyl, acyl-alkyl with linear or branched $C_1$-$C_{18}$ alkyl, acyl-alkenyl or acyl-alkynyl with linear or branched $C_2$-$C_{18}$ alkenyl and alkynyl, acyl-aryl, acyl-heteroaryl, and acyl-amine, wherein said aryl and heteroaryl groups are optionally substituted by one or more groups selected from $C_1$-$C_3$ alkyl, carboxyl, and acyl-alkyl with $C_1$-$C_3$ alkyl;

or $R_{12}$ and $R_{13}$ together form a pyrrole ring optionally substituted by one or more $C_1$-$C_3$ alkyl groups;

and wherein m is an integer from 1 to 4, and n, o, p are, independently of one another, an integer from 1 to 12.

In a particularly preferred embodiment, the pyrrole derivatives used to prepare the adducts are represented by formula (1a)

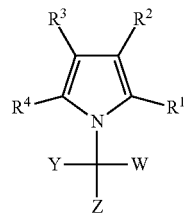

wherein $R_1$, $R_2$, $R_3$, and $R_4$ are independently selected in the group consisting of: hydrogen and linear or branched $C_1$-$C_3$ alkyl;

W and Y are independently selected from the group consisting of: hydrogen and linear or branched $C_1$-$C_3$ alkyl; and Z is represented by one of the formulae (II)-(III) below

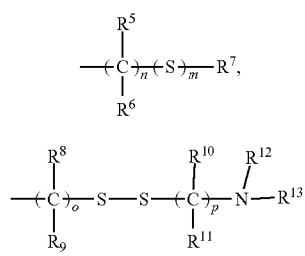

wherein $R_5$, $R_6$, $R_8$, $R_9$, $R_{10}$, and $R_{11}$ are represented by hydrogen or linear or branched $C_1$-$C_3$ alkyl; and $R_7$, $R_{12}$ and $R_{13}$ are independently selected from the group consisting of: hydrogen, linear or branched $C_1$-$C_{18}$ alkyl, acyl-alkyl with linear or branched $C_1$-$C_{18}$ alkyl, acyl-alkenyl with linear or branched $C_2$-$C_{18}$ alkenyl, and acyl-aryl wherein said aryl group is optionally substituted by one or more carboxyl groups;

or $R_{12}$ and $R_{13}$ together form a pyrrole ring optionally substituted by one or more $C_1$-$C_3$ alkyl groups;

and wherein m is 1, and n, o, p are, independently of one another, an integer from 1 to 4.

According to an alternative embodiment of the present invention, the pyrrole derivatives used to prepare the adducts are represented by formula (1b)

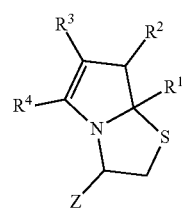

wherein $R_1$, $R_2$, $R_3$, and $R_4$ are independently selected in the group consisting of: hydrogen, linear or branched $C_1$-$C_{22}$ alkyl, linear or branched $C_2$-$C_{22}$ alkenyl or alkynyl, aryl, linear or branched $C_1$-$C_{22}$ alkyl-aryl, linear or branched $C_2$-$C_{22}$ alkenyl-aryl, linear or branched $C_2$-$C_{22}$ alkynyl-aryl, and heteroaryl; and Z is selected from the group consisting of: hydrogen, linear or branched $C_1$-$C_{18}$ alkyl, linear or branched $C_2$-$C_{18}$ alkenyl or alkynyl, and the formulae (II)-(V) below

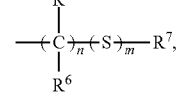

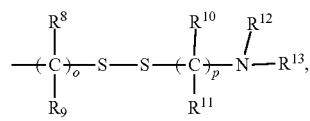

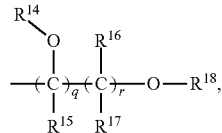

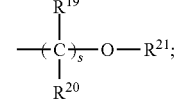

wherein $R_5$, $R_6$, $R_7$, $R_8$, $R_9$, $R_{10}$, $R_{11}$, $R_{12}$, $R_{13}$, $R_{14}$, $R_{15}$, $R_{16}$, $R_{17}$, $R_{18}$, $R_{19}$, $R_{20}$, and $R_{21}$ are independently selected from the group consisting of: hydrogen, linear or branched $C_1$-$C_{18}$ alkyl, linear or branched $C_2$-$C_{18}$ alkenyl or alkynyl, aryl, linear or branched $C_1$-$C_{22}$ alkyl-aryl, linear or branched $C_2$-$C_{22}$ alkenyl-aryl, linear or branched $C_2$-$C_{22}$ alkynyl-aryl, heteroaryl, carboxyl, acyl-alkyl with linear or branched $C_1$-$C_{18}$ alkyl, acyl-alkenyl or acyl-alkynyl with linear or branched $C_2$-$C_{18}$ alkenyl and alkynyl, acyl-aryl, acyl-heteroaryl, and acyl-amine, wherein said aryl and heteroaryl groups are optionally substituted by one or more groups selected from $C_1$-$C_3$ alkyl, carboxyl, and acyl-alkyl with $C_1$-$C_3$ alkyl;

or $R_{12}$ and $R_{13}$ together form a pyrrole ring;

and wherein m is an integer from 1 to 4, and n, o, p, q, r, and s are, independently of one another, an integer from 1 to 12.

Preferably, according to this alternative embodiment, the pyrrole derivatives used to prepare the adducts are represented by formula (1 b)

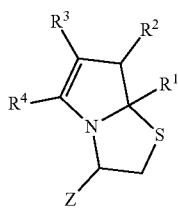

wherein $R_1$, $R_2$, $R_3$, and $R_4$ are independently selected in the group consisting of: hydrogen, linear or branched $C_1$-$C_{22}$ alkyl, linear or branched $C_2$-$C_{22}$ alkenyl or alkynyl, aryl, linear or branched $C_1$-$C_{22}$ alkyl-aryl, linear or branched $C_2$-$C_{22}$ alkenyl-aryl, linear or branched $C_2$-$C_{22}$ alkynyl-aryl, and heteroaryl; and Z is selected from the group consisting of: hydrogen, linear or branched $C_1$-$C_{18}$ alkyl and linear or branched $C_2$-$C_{18}$ alkenyl or alkynyl.

According to a further alternative embodiment of the present invention, the pyrrole derivatives used to prepare the adducts are represented by formula (1c)

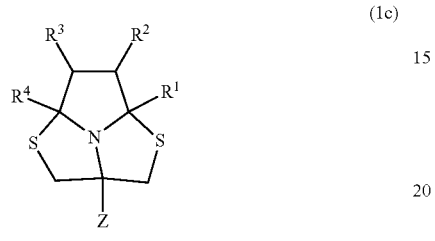

wherein $R_1$, $R_2$, $R_3$, and $R_4$ are independently selected in the group consisting of: hydrogen, linear or branched $C_1$-$C_{22}$ alkyl, linear or branched $C_2$-$C_{22}$ alkenyl or alkynyl, aryl, linear or branched $C_1$-$C_{22}$ alkyl-aryl, linear or branched $C_2$-$C_{22}$ alkenyl-aryl, linear or branched $C_2$-$C_{22}$ alkynyl-aryl, and heteroaryl; and Z is selected from the group consisting of: hydrogen, linear or branched $C_1$-$C_{18}$ alkyl, linear or branched $C_2$-$C_{18}$ alkenyl or alkynyl, and the below formulae (II)-(V)

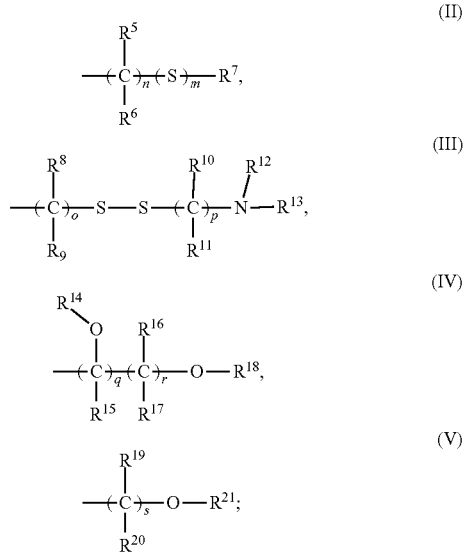

wherein $R_5$, $R_6$, $R_7$, $R_8$, $R_9$, $R_{10}$, $R_{11}$, $R_{12}$, $R_{13}$, $R_{14}$, $R_{15}$, $R_{16}$, $R_{17}$, $R_{18}$, $R_{19}$, $R_{20}$, and $R_{21}$ are independently selected from the group consisting of: hydrogen, linear or branched $C_1$-$C_{18}$ alkyl, linear or branched $C_2$-$C_{18}$ alkenyl or alkynyl, aryl, linear or branched $C_1$-$C_{22}$ alkyl-aryl, linear or branched $C_2$-$C_{22}$ alkenyl-aryl, linear or branched $C_2$-$C_{22}$ alkynyl-aryl, heteroaryl, carboxyl, acyl-alkyl with linear or branched $C_1$-$C_{18}$ alkyl, acyl-alkenyl or acyl-alkynyl with linear or branched $C_2$-$C_{18}$ alkenyl and alkynyl, acyl-aryl, acyl-heteroaryl, and acyl-amine, wherein said aryl and heteroaryl groups are optionally substituted by one or more groups selected from $C_1$-$C_3$ alkyl, carboxyl, and acyl-alkyl with $C_1$-$C_3$ alkyl;

or $R_{12}$ and $R_{13}$ together form a pyrrole ring;

and wherein m is an integer from 1 to 4, and n, o, p, q, r, and s are, independently from one another, an integer from 1 to 12.

Preferably, according to this alternative embodiment, the pyrrole derivatives used to prepare the adducts are represented by formula (1c)

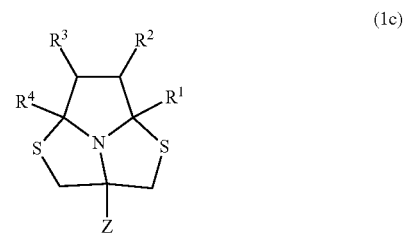

wherein $R_1$, $R_2$, $R_3$, and $R_4$ are independently selected in the group consisting of: hydrogen, linear or branched $C_1$-$C_{22}$ alkyl, linear or branched $C_2$-$C_{22}$ alkenyl or alkynyl, aryl, linear or branched $C_1$-$C_{22}$ alkyl-aryl, linear or branched $C_2$-$C_{22}$ alkenyl-aryl, linear or branched $C_2$-$C_{22}$ alkynyl-aryl, and heteroaryl; and Z is selected from the group consisting of: hydrogen, linear or branched $C_1$-$C_{18}$ alkyl and linear or branched $C_2$-$C_{18}$ alkenyl or alkynyl.

According to a particularly preferred embodiment, the pyrrole derivative of formula (1a) is selected in the group comprising:

2-(2,5-dimethyl-1H-pyrrol-1-yl)ethan-1-thiol, 1,2-bis(2-(2,5-dimethyl-1H-pyrrol-1-yl)ethyl) disulphide, S-(2-(2,5-dimethyl-1H-pyrrol-1-yl)ethyl) ethanethioate, S-(2-(2,5-dimethyl-1H-pyrrol-1-yl)ethyl) prop-2-enethioate, S-(2-(2,5-dimethyl-1H-pyrrol-1-yl)ethyl) 2-methylprop-2-enethioate, 2-((2-(2,5-dimethyl-1H-pyrrol-1-yl)ethyl)disulphanyl)-N,N-dimethylethan-1-amine, S-(2-(2,5-dimethyl-1H-pyrrol-1-yl)ethyl) octadecanethioate; and 2-(((2-(2,5-dimethyl-1H-pyrrol-1-yl)ethyl)thio)carbonyl) benzoic acid, and mixtures thereof.

The pyrrole derivatives used to prepare the adducts according to the present invention can be prepared according to methods known in the art (see for example Barbera, Vincenzina, et al. "Facile and sustainable functionalization of graphene layers with pyrrole compounds." *Pure and Applied Chemistry* 90.2 (2018): 253-270).

In brief, a suitable primary amine is reacted with a diketone of general formula:

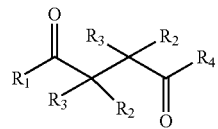

wherein $R_1$, $R_2$, $R_3$, $R_4$ are independently selected in the group consisting of: hydrogen, linear or branched $C_1$-$C_{22}$ alkyl, linear or branched $C_2$-$C_{22}$ alkenyl or alkynyl, aryl, linear or branched $C_1$-$C_{22}$ alkyl-aryl, linear or branched $C_2$-$C_{22}$ alkenyl-aryl, linear or branched $C_2$-$C_{22}$ alkynyl-aryl, and heteroaryl.

Particularly preferred are the adducts formed between pyrrole derivatives comprising at least one sulphur atom of formula 1a) as represented above and the $sp^2$ hybridized carbon allotropes selected in the group comprising: carbon black, fullerene, single wall or multiwall carbon nanotubes, graphene with 2 layers (bi-layer graphene), graphene with few layers (from 3 to 10; few layer graphene), graphite (for example with a number of graphene layers lying between 10 and 10,000) and single wall or multiwall carbon nanotubes, in particular high surface area graphite and mixtures thereof.

More preferably, the adducts between $sp^2$ hybridized carbon allotropes and pyrrole derivatives according to the present invention are selected in the group comprising adducts between carbon black and pyrrole derivatives of formula 1a), between high surface area graphite and pyrrole derivatives of formula 1a), and between single wall or multiwall carbon nanotubes and pyrrole derivatives of formula 1a).

Still more preferably, the adducts according to the invention are adducts between an $sp^2$ hybridized carbon allotrope selected from carbon black, high surface area graphite, graphene with 2 layers (bi-layer graphene), graphene with few layers (from 3 to 10; few layer graphene), and single wall or multiwall carbon nanotubes, and a pyrrole derivative of formula 1a) selected in the group comprising: 2-(2,5-dimethyl-1H-pyrrol-1-yl)ethan-1-thiol, 1,2-bis(2-(2,5-dimethyl-1H-pyrrol-1-yl)ethyl) disulfide, S-(2-(2,5-dimethyl-1H-pyrrol-1-yl)ethyl ethanethionate, S-(2-(2,5-dimethyl-1H-pyrrol-1-yl)ethyl prop-2-enethionate, S-(2-(2,5-dimethyl-1H-pyrrol-1-yl)ethyl) 2-methylprop-2-enethionate, 2-((2-(2,5-dimethyl-1H-pyrrol-1-yl)ethyl)disulphanyl)-N,N-dimethylethan-1-amine, S-(2-(2,5-dimethyl-1H-pyrrol-1-yl)ethyl octadecanethionate; and 2-(((2-(2,5-dimethyl-1H-pyrrol-1-yl)ethyl)thio)carbonyl) benzoic acid.

Preferably, the adducts are characterized by a weight ratio between allotrope and pyrrole derivative comprised from 100:1 to 1:10, still more preferably from 100:1 to 1:1.

Carbon allotropes, due to the fact that they are more or less reactive aromatic systems, can form various types of intermolecular interaction both of the covalent type and via more labile intermolecular interactions.

Without being bound by any theory, in the adduct formation reaction, the following two types of interaction can be hypothesized:

(i) π-π interaction: an interaction which can exist between systems which possess π electrons, thus having $sp^2$ or sp hybridization. The interaction is between a pair of π electrons and a σ orbital, or between the electrons of a σ orbital and a π orbital, or again between the electrons of two π orbitals. This type of adduct is also known as a "π complex" and is characterized by so-called stacking, i.e. a stacked arrangement of the aromatic molecules.

(ii) covalent bonds between the compound of formula (1) and the carbon allotrope, via reactions typical of polycyclic aromatic systems such as for example: 1,3-dipolar cycloadditions, Diels-Alder reaction.

The adduct formation can also take place via the interaction between the functional groups of the pyrrole derivative of formula (1) and the functional groups possibly present on the carbon allotrope. These interactions can be of an intermolecular nature, such as hydrogen bonds and dipole interactions, or of a covalent nature such as for example an esterification via reaction with an acidic group.

The implementation of this interaction (whether of intermolecular or covalent nature) can also be effected solely by input of energy (for example mechanical or thermal energy, or by photon irradiation) without the use of solvents.

A second aspect of the present invention is therefore a process for obtaining the adducts between $sp^2$ hybridized carbon allotropes and the pyrrole derivatives comprising at least one sulphur atom according to the present invention, said process comprising the steps of:

a) forming a mixture of at least one compound of formula (1) and of at least one $sp^2$ hybridized carbon allotrope; and b) supplying energy to the mixture obtained to effect an interaction between the compound of formula (1) and the allotrope, obtaining the adduct between $sp^2$ hybridized carbon allotrope and the pyrrole derivative.

Optionally, the adduct is separated from non-interacted carbon allotropes and/or pyrrole derivatives, with methods known by the skilled in the art.

The energy transfer of step b) of the process according to the present invention is performed in order to improve the interaction between the compound of formula (1) and the carbon allotrope. In the absence of energy transfer, this interaction would be weaker and could lead to the partial release of the compound of formula (1) from the carbon allotrope, in particular if the adduct is in an environment of a polar nature.

The energy forms which can be transferred to the composition to contribute to the adduct formation are: mechanical energy, thermal energy, photons, or a combination of two or more of these energy forms.

Mechanical Energy

The mechanical treatment can for example consist in placing the powder obtained (allotrope/compound of formula (1)) in a ball mill, for example comprising a jar equipped with stainless steel spheres. Once closed, the jar is placed in a planetary mixer and is left to rotate at a rate from 200 to 500 rpm for periods from 1 to 360 minutes. Immediately afterwards, the powder is transferred.

The mechanical treatment is used both to promote the separation of the carbon allotropes into their fundamental components (for example exfoliation in the case of graphite), and to favour the relative dispersion of the allotrope and of the compound of formula (1), in order to obtain a better distribution of the compound of formula (1) on the allotrope, and to induce the formation of a more stable interaction.

Thermal Energy

The thermal treatment can for example consist in placing the powder obtained (carbon allotrope/compound of formula (1)) in a reaction flask equipped with a condenser, or in a closed vessel. Once the reactor has been placed on a heating plate, the reaction is carried out at temperatures of from 130 to 180° C. The heating is maintained for a time from 15 and 360 minutes.

Photons

The photon treatment can for example consist in placing the powder obtained (carbon allotrope/compound of formula (1)) in a laboratory crystallizer forming a thin layer or in placing the powder in a closed quartz vial. Once the reactor has been set up within a closed chamber equipped with a 254 nm low-pressure mercury, lamp (or using a Rayonet® reactor equipped with the same type of reactor) the mixture is irradiated for times variable from 30 to 180 minutes. At the end of this time, the mixture is transferred and analysed.

In one embodiment, the process for obtaining the adducts between $sp^2$ hybridized carbon allotropes and pyrrole derivatives according to the present invention comprises the steps of:
  i) obtaining a solution of at least one compound of formula (1) in a polar protic or aprotic solvent selected in the group consisting of: water, alcohols, carbonyl solvents such as acetone, esters such as ethyl acetate, dimethyl sulfoxide, acetonitrile, ethers, or mixtures thereof;
  ii) obtaining a suspension of the carbon allotrope in the polar protic or aprotic solvent used for the preparation of the solution in step i);
  iii) mixing said solution and said suspension by mechanical or magnetic stirring or by sonication;
  iv) removing said solvent from the mixture obtained in step iii); and
  v) supplying thermal and/or mechanical energy and/or energy by irradiation with photons to the mixture obtained in step iv), in presence of air or oxygen.

Preferably the thermal energy is supplied at a temperature of from 50 to 180° C., for example for a time of from 15 to 360 minutes.

Preferably the mechanical energy is supplied for a time of from 1 to 360 minutes.

Preferably the energy for irradiation with photons is supplied at a wavelength of from 200 to 380 nm, for example for a time of from 30 to 180 minutes.

The process according to this embodiment makes it possible to obtain a homogeneous dispersion of the carbon allotrope and of at least one compound of formula (1) and thus a homogeneous dispersion of the compound of formula (1) in the carbon-based filler.

Preferably the solvent of step i) is an eco-compatible solvent, for example water.

Alternatively the preparation of the adduct can be effected without previous preparation of the mixture and/or of the suspension according to the aforesaid steps i) and ii) but simply by mixing the two components and supplying energy.

The process of solvent removal from the mixture obtained (step iv) can occur by means of any suitable method for solvent removal, such as for example evaporation under vacuum, spray-drying, etc.

A further aspect of the present invention is represented by a crosslinkable elastomer composition comprising the adducts between $sp^2$ hybridized carbon allotropes and pyrrole derivatives with at least one sulphur atom according to the present invention, as described above.

The elastomer compositions according to the present invention comprise at least one unsaturated elastomer selected in the group consisting of: poly(1,4-cis-isoprene), either natural rubber or synthetic polymer, poly(3,4-isoprene), poly(butadiene) (in particular poly(butadiene) with a high content of 1,4-cis units), isoprene/isobutene copolymers, halogenated isoprene/isobutene copolymers such as for example halogenated butyl rubber, in particular chlorobutyl and bromobutyl rubber, 1,3-butadiene/acrylonitrile copolymers, styrene/1,3-butadiene copolymers, styrene/isoprene/1,3-butadiene copolymers, styrene/1,3-butadiene/acrylonitrile copolymers, or mixtures thereof.

The elastomer compositions according to the present invention can further contain at least one elastomer of one or more mono-olefins. The mono-olefins can be selected from: ethylene and 1-olefins with 3 to 12 carbon atoms, such as, for example, propylene, 1-butene, 1-pentene, 1-hexene, 1-octene, or mixtures of these mono-olefins.

The elastomer of one or more mono-olefins can contain a diene, which generally has from 4 to 20 carbon atoms and is preferably selected from: 1,3-butadiene, isoprene, 1,4-hexadiene, 1,4-cyclohexadiene, 5-ethylidene-2-norbornene, 5-methylene-2-norbornene, vinylnorbornene or mixtures of these dienes. The diene can optionally be halogenated.

Among these elastomers of one or more mono-olefins, the following are preferred: ethylene/propylene copolymers (EPR) or ethylene/propylene/diene copolymers (EPDM) and poly(isobutene).

The elastomer compositions can further contain an unsaturated, diene or non-diene monomers based elastomer, functionalized by reaction with a suitable terminating agent or coupling agents. In particular, the diene elastomer polymer can be obtained by anionic polymerization promoted by an organometallic initiator (in particular an alkyl-lithium) and terminated by reaction with suitable terminating agents or coupling agents such as, for example, epoxides, carbonyl compounds such as for example cyclohexanone and benzophenone, substituted or unsubstituted, imines, carbodiimides, alkyl-tin halides, alkoxysilanes or aryloxysilanes.

Preferably, the crosslinkable elastomer composition contains an amount of adducts between $sp^2$ hybridized carbon allotropes and pyrrole derivatives according to the present invention, comprised from 5 to 100 phr, more preferably from 10 to 80 phr.

According to a preferred embodiment, said elastomer composition also contains further reinforcing fillers selected in the group comprising: carbon black, silica, layer silicates, mixed oxides of aluminium and magnesium with lamellar structure, alumina, and silico aluminates.

Particularly preferred is amorphous silica, which can be of natural origin, such as diatomite, or synthetic for example precipitated silica, silica gel, pyrogenic silica, or silica subjected to surface treatments.

Preferably, in the elastomer composition according to the present invention, the total amount of reinforcing fillers, understood to mean the sum of the amount of adducts according to the present invention and further reinforcing fillers, is comprised from 20 to 150 phr, more preferably from 40 to 80 phr.

Advantageously, said crosslinkable elastomer composition contains a vulcanizing agent and the vulcanization takes place according to the known techniques, in particular with vulcanization systems based on sulphur commonly used per for diene elastomer polymers. For this purpose, in the materials, after one or more steps of thermal-mechanical treatment, a vulcanizing agent based on sulphur is incorporated together with vulcanization accelerators. At the final treatment step, the temperature is generally maintained below 120° C. and preferably below 100° C., so as to avoid any undesired pre-crosslinking phenomenon.

Preferably, the vulcanizing agent comprises vulcanization systems based on sulphur, comprising sulphur or molecules comprising sulphur (sulphur donors), together with vulcanization accelerators and/or activators known in the art.

The activators which are particularly effective are compounds of zinc and in particular ZnO, $ZnCO_3$ and zinc salts of saturated or unsaturated fatty acids comprising from 8 to 18 carbon atoms, such as, for example, zinc stearate, which are preferably formed in situ in the elastomer composition from ZnO and fatty acid, or mixtures thereof.

The accelerators which are commonly used can be selected from: dithiocarbamates, guanidine, thiourea, thiazoles, sulfenamides, thiurams, amines and xanthates or mixtures thereof.

Preferred vulcanising agents are for example, stearic acid, ZnO, 6PPD (1,3-dimethylbutyl)-N'-phenyl-p-phenylenediamine), TBBS (N-tert-butyl-2-benzothiazyl sulfenamide) and sulphur or mixtures thereof.

According to a preferred embodiment, said crosslinkable elastomer composition contains a quantity of vulcanizing agent greater than or equal to about 1 phr, preferably greater than or equal to about 2 phr.

Preferably, the quantity of vulcanizing agent is less than or equal to about 7.5 phr, preferably less than or equal to about 7.

Advantageously the quantity of sulphur lies between about 0.5 phr and about 6.5 phr.

Said elastomer composition can contain other commonly used additives, selected on the basis of the specific application for which the composition is intended. For example, to said materials can be added: antioxidants, anti-ageing agents, plasticizers, adhesives, anti-ozone agents, modifying resins, or mixtures thereof.

In particular, for the purpose of improving workability, a plasticizer generally selected from mineral oils, plant oils, synthetic oils or mixtures thereof, such as, for example, aromatic oil, naphthenic oil, phthalates, soya oil or mixtures thereof can be added to said elastomer composition. The amount of plasticizer is generally from 0 phr to about 70 phr, preferably from about 5 phr to about 30 phr.

The elastomer composition can be prepared by mixing together the polymeric components with the adducts between the $sp^2$ hybridized carbon allotropes and the pyrrole derivatives, according to the present invention, and together with the other reinforcing fillers and the other additives possibly present, according to techniques known in the art.

The mixing can be performed, for example, using an open mixer of the "open-mill" type and/or an internal mixer of the type with tangential rotors (Banbury®), and/or with intermeshing rotors (Intermix™), and/or in continuous mixers of the Ko-Kneader™ type, and/or of the twin screw or multi-screw type and/or of the planetary type.

The components of the elastomer composition are not generally introduced all simultaneously into the mixer but are typically added in sequence. In particular, the vulcanization additives, such as the vulcanizing agent and possibly the accelerants and the retardants, are usually added in a downstream step relative to the incorporation and processing of all the other components.

In the vulcanizable or final vulcanized elastomer composition, the individual components of the elastomer composition do not always remain unaltered or are individually traceable in that they may be transformed, completely or in part, by effect of the interaction with other components, heat and/or mechanical processing. The term "elastomer composition" is here understood to include the totality of all the components which are added in the preparation of the elastomer mixture, independently of the fact that these may all actually be present simultaneously, that they may be introduced sequentially or that they may then be traceable in the elastomer mixture or in the final tyre.

A further aspect of the present invention is represented by a tyre for vehicle wheels comprising at least one structural element comprising a crosslinked elastomer material obtained by crosslinking of a crosslinkable elastomer composition according to the present invention.

In particular, said tyre comprises at least one carcass structure having opposite lateral edges associated with respective annular reinforcing structures, a belt structure applied in a position radially external relative to said carcass structure, a tread band applied in a position radially external to said carcass structure, and a pair of sidewalls applied laterally on opposite sides relative to said carcass structure.

Advantageously, said structural element is selected in the group consisting of tread band, sidewall, sidewall insert, layers of elastomer material radially internal relative to said tread band, for example, cushion and mini-sidewall, bead filler, and rubber coating of the textiles and the metals. In a particularly preferred embodiment, the structural element is the tread band.

Such structural elements, in particular the tread band, can be advantageously prepared with the elastomer composition comprising adducts between an $sp^2$ hybridized carbon allotrope and a pyrrole derivative according to the present invention, characterized by low hysteresis and a reduced Payne effect, thus obtaining a clear advantage on the road-holding and in general on the performance of the tyre, such as the resistance to the deformation due for example to an increase in the temperature.

Furthermore, the aforesaid elastomer composition comprising adducts between a $sp^2$ hybridized carbon allotrope and a pyrrole derivative can prove to be electrically conductive, contributing to creating a conductive path between the rim and the ground.

The tyre according to the invention can be used on vehicles with two, three or four wheels, or on heavy vehicles, or on light transport vehicles.

The tyre according to the invention can be for summer or winter use or for all seasons.

The tyre according to the present invention can be manufactured according to a process comprising:
  assembling components of a raw tyre on at least one building drum;
  shaping, moulding and vulcanizing the tyre;
  wherein at least one component of the raw tyre contains the vulcanizable elastomer composition as previously described.

The term "raw" is generally used to indicate a material, a composition, a component or a tyre not yet vulcanized.

The finishing of the tyres can be effected by assembly of respective semi-finished products on a moulding drum, not illustrated, by means of at least one assembly device.

At least a part of the components intended to form the carcass structure of the tyre can be constructed and/or assembled on the building drum. More particularly, the building drum is ready to receive firstly the liner, if any, then the carcass structure and the anti-abrasive strip. Then, devices not illustrated coaxially engage one of the annular anchoring structures around each of the terminal edges, place an external sleeve comprising the belt structure and the tread band in a position coaxially centred around the cylindrical carcass sleeve and shape the carcass sleeve according to a toroidal configuration by means of a radial dilatation of the carcass structure, such as to bring about its application against a radially internal surface of the external sleeve.

Following the manufacture of the raw tyre, a moulding and vulcanization treatment is performed in order to effect the structural stabilization of the tyre via crosslinking of the elastomer mixture, and also to impress a desired tread design on the tread band and to impress possible distinctive graphic signs on the sidewalls.

FIG. 1 illustrates in radial half-section a tyre for vehicle wheels according to the invention.

In FIG. 1, "a" indicates an axial direction and "X" indicates a radial direction, in particular X-X indicates the trace of the equatorial plane.

For simplicity, FIG. 1 shows only one portion of the tyre, the remaining portion not represented being identical and positioned symmetrically relative to the equatorial plane "X-X".

The tyre 100 for four-wheeled vehicles comprises at least one carcass structure, comprising at least one carcass layer 101 presenting mutually opposite terminal edges bonded to respective annular anchoring structures 102, called bead cores, possibly combined with a bead filler 104.

The zone of the tyre comprising the bead core 102 and the filler 104 forms a bead structure 103 intended for the anchoring of the tyre on a corresponding mounting rim, not illustrated.

The carcass structure is usually of the radial type, namely the reinforcing elements of at least one carcass layer 101 lie essentially on planes comprising the axis of rotation of the tyre and essentially perpendicular to the equatorial plane of the tyre. Said reinforcing elements are generally represented by textile cords, for example rayon, nylon or polyester (for example polyethylene naphthalate PEN). Each bead structure is connected to the carcass structure by folding behind opposite lateral edges of the at least one carcass layer 101 around the annular anchoring structure 102, so as to form the so-called carcass turnups 101a.

In one embodiment, the coupling between carcass structure and bead structure can be provided via a second carcass layer, not represented in FIG. 1, applied in an axially external position relative to the first carcass layer.

An anti-abrasive strip 105 possibly implemented with an elastomer composition according to the invention is arranged in a position external to each bead structure 103.

To the carcass structure, a belt structure 106 comprising one or more belt layers 106a, 106b placed in radial superposition relative to one another and to the carcass layer, having typically textile or metal reinforcing cords incorporated within one layer of vulcanized elastomer material is associated.

Such reinforcing cords can have a crossed orientation relative to a circumferential development direction of the tyre 100. "Circumferential" direction is understood to mean a direction generally oriented in the direction of rotation of the tyre.

In a position radially more external to the belt layers 106a, 106b at least one reinforcing layer at zero degrees 106c can be applied, commonly known as "0° belt", which typically incorporates a plurality of elongated reinforcing elements, typically metal or textile cords, oriented in an essentially circumferential direction, thus forming an angle of a few degrees (for example an angle between about 0° and 6°) relative to a direction parallel to the equatorial plane of the tyre, and coated with vulcanized elastomer material.

In a position radially external to the belt structure 106, a tread band 109 in vulcanized elastomer material is applied.

Further, on the lateral surfaces of the carcass structure, each extending from one of the lateral edges of the tread 109 up to where it coincides with the respective bead structure 103, respective sidewalls 108 in vulcanized elastomer material are applied at an axially external position.

In a radially external position, the tread band 109 has a rolling surface 109a intended to make contact with the ground. Circumferential grooves, which are connected by transverse indentations (not shown in FIG. 1) such as to define a plurality of small blocks of various forms and dimensions distributed on the rolling surface 109a, are generally implemented in this surface 109a, which for simplicity is shown smooth in FIG. 1.

An underlayer 111 in vulcanized elastomer material can be positioned between the belt structure 106 and the tread band 109.

A strip of the elastomer composition 110, commonly known as "mini-sidewall", in vulcanized elastomer material can optionally be present in the connecting zone between the sidewalls 108 and the tread band 109, this mini-sidewall being generally obtained by co-extrusion with the tread band 109 and allowing an improvement in the mechanical interaction between the tread band 109 and the sidewalls 108. Preferably the end portion of the sidewall 108 directly covers the lateral edge of the tread band 109.

In the case of tyres with no inner tube, a layer of rubber 112, generally known as a "liner", which provides the necessary impermeability to the air inflating the tyre, can also be provided in a radially internal position relative to the carcass structure 101.

The rigidity of the tyre 108 in the radial direction can be improved by endowing the bead structure 103 with a reinforcing layer 120 generally known as a "flipper" or strip additional insert.

The flipper 120 is a reinforcing layer which is wound around the respective bead core 102 and the bead filler 104 so as to at least partially surround them.

The flipper 120 typically comprises a plurality of textile cords, incorporated within a layer of vulcanized elastomer material.

The tyre bead structure 103 can contain a further protective layer which is generally known by the term "chafer" 121 or protective strip and which has the function of further increasing the rigidity and/or integrity of the bead structure 103.

The chafer 121 usually comprises a plurality of cords incorporated within a rubber coating layer of vulcanized elastomer material. Such cords are generally implemented in textile materials (for example aramid or rayon) or in metallic materials (for example steel cords).

A layer or sheet of elastomer material can be positioned between the belt structure and the carcass structure (not shown in FIG. 1). The layer can have a uniform thickness. Alternatively, the layer can have a thickness variable in the axial direction. For example, the layer can have a maximum thickness close to its axially external edges relative to the central (crown) zone.

Advantageously the layer or sheet can extend over an area substantially corresponding to the development surface of said belt structure.

In a preferred embodiment, a layer or sheet of elastomer material as described above can be placed between the belt structure and the tread band, where said supplementary layer or sheet preferably extends over an area substantially corresponding to the development surface of the belt structure.

The present invention will be further illustrated hereinafter by means of a number of examples, which are provided for purely illustrative purposes and without any limitation of this invention.

EXPERIMENTAL SECTION

Materials

All the reagents and solvents were obtained from Sigma-Aldrich and used without further purification: 2,5-hexanedione (MW=114.12 g/mol); 2-amino-1,3-propanediol (MW=91.10 g/mol); acetone (≥97%); O-(2-aminopropyl)-O'-(2-methoxyethyl)polypropylene glycol (average Mn 600); and 2-aminoethanethiol hydrochloride (MW=113.61 g/mol). The $^1$H-NMR spectra were recorded on samples dissolved in deuterated chloroform (CDCl$_3$) and dimethyl sulfoxide (DMSO-d$_6$).

The elastomers used are:

Poly(styrene-co-butadiene) (S-SBR) from polymerization in solution with anionic catalysis. 25% by weight of styrene, 61.7% of vinyls (out of total butadiene). Mooney viscosity (ML(1+4, 100° C.): 55 MU, Tg:—28° C.;

Poly(1,4-cis-isoprene) of natural origin, natural rubber (NR), from *Hevea brasiliensis*: STR20. From Eatern GR Thailand—Chonburi. Mooney viscosity (ML(1+4) @ 100° C.): 73 MU. Solid natural rubber, SIR20, from Eatern GR Thailand—Chonburi. Mooney viscosity (ML(1+4) @ 100° C.): 73 MU;

Nitrile rubber Nipol® DN 219 (NBR). From ZEON CORPORATION. Mooney viscosity (ML(1+4) @ 100° C.): 22-32 MU).

The carbon allotropes used are:

Carbon black N 234 from Cabot Corporation. Carbon 98% by weight; surface area 113 m$^2$/g, average size of the individual particles: 27 nm; average size of the aggregates 152 nm;

High surface area graphite (HSAG) Nano 27 from Asbury. Carbon ≥99% by weight; surface area 250 m$^2$/g, elemental analysis (U.S. Standard Test Sieves): carbon 99.82%, ash 0.18%, moisture 0.97%. Ingredients for the preparation of the elastomer compositions:

ZnO (zinc oxide),
stearic acid (Sogis),
6PPD ((1,3-dimethylbutyl)-N'-phenyl-p-phenylenediamine) from Crompton,
S (sulphur) from Solfotecnica,
TBBS (N-tert-butyl-2-benzothiazyl sulphenamide) from Flexsys,
CBS (N-cyclohexyl-2-benzothiazole sulphenamide) from Westco,
TDAE (treated distillate aromatic extracted oil) Vivatec 500 (Hansen & Rosenthal KG),
RIOWAX BM01 (wax from SER WAX INDUSTRY),
paraffin oil (from Sigma-Aldrich) and
Agerite resin D (from Vanderbilt Minerals).

Characterization

The pyrrole compounds obtained were analysed by NMR spectroscopy. The $^1$H-NMR and $^{13}$C-NMR spectra were recorded with a Bruker 400 MHz (100 MHz $^{13}$C) instrument operating at 298 K. The chemical shifts are stated in parts per million (ppm) with the solvent residues peaks as internal standard (DMSO-d$_6$: δH=2.50 ppm, CDCl$_3$: δH=7.26 ppm).

The adducts between carbon allotropes and the pyrrole compounds were characterized by the following techniques.

Thermogravimetric analysis (TGA) is a quantitative analytical technique which provides the weight loss of the material analysed as a function of time and temperature. In other words, the material is heated with a given heating regime and can undergo transformations which lead to the loss of part or all of the material itself, which passes into the vapour phase. The TGA under a current of N$_2$ (60 mL/min) was performed using a Mettler TGA SDTA/851 instrument in accordance with the standard method ISO9924-1. The samples (10 mg) were heated from 30 to 300° C. at 10° C./min, maintaining at 300° C. for 10 min, and immediately afterwards heating to 550° C. (20° C./min). After having maintained them 550° C. for 15 min, further heating to 650° C. follows at a rate of 30° C./min and maintaining at 650° C. for 20 min under a current of air (60 mL/min).

The functionalization yield of the adducts obtained, i.e. the percentage quantity by weight of molecule bound to the sp$^2$ hybridized carbon allotrope, was calculated using the following equation:

$$\text{Functionalization yield}(\%) = 100 * \frac{\text{compound of formula (1) by weight in (adduct[compound of formula (1) – CA adduct]) after purification}}{\text{compound of formula (1) by weight in (adduct[compound of formula (1) – CA adduct]) pre – purification}}$$

The values stated for the purposes of the calculation make reference to the quantity of pyrrole compound, contained in the adducts, determined by TGA before and after the purification procedure and make reference to the % weight losses determined from the TGA graph in the temperature range which runs from 0 to 900° C.

The elastomer compositions were vulcanized and characterized by the following procedures and techniques.

The crosslinking was performed with a Monsanto RPA 2000 rheometer, at 170° C. with a frequency of 1.667 Hz and an angle of 6.98% (0.5 rad), for 20 and 10 minutes.

The static mechanical properties were measured at 23° C. in accordance with the standard ISO 37:2005. In particular, the load was measured at different levels of elongation, 50%, 100% and 300%, named in sequence $\sigma_{50}$, $\sigma_{100}$, $\sigma_{300}$, and the load at break and the elongation at break named in sequence $\sigma_B$ and $\varepsilon_B$. The tensile tests were performed on test pieces of the dumbbell type with rectilinear axis.

The dynamic mechanical properties were measured by applying a dynamic stress via shear stress, at constant frequency and at constant temperature, increasing the deformation amplitude. The test was performed with a Monsanto RPA 2000 rheometer. The samples of elastomer material composition were held in the rheometer at 50° C. for 90 seconds, the stress was then applied at 50° C. in the deformation amplitude range between 0.1% and 25%, with a frequency of 1 Hz, increasing the deformation amplitude in the range stated above. This treatment is performed to eliminate the "previous thermo-mechanical history". The vulcanization was then performed at 170° C. for 20 minutes, with a frequency of 1.667 Hz and an angle of 6.98% (0.5 rad). The vulcanized sample was left in the instrument for 10 minutes at 50° C.

The sinusoidal stress was then applied with the same conditions already stated, at 50° C. The sinusoidal stress is then again applied, always with the same experimental conditions. Curves are then obtained which state the value of the moduli as a function of the deformation amplitude. Such moduli are illustrated below. The G' modulus is the elastic modulus. The G" modulus is the viscous modulus. The ratio G"/G' is stated as Tan Delta. From the strain sweep test, the values of the following parameters are obtained: G'γ=0.28% which is the value of G' at minimum deformation, ΔG' which is the difference between the value of G' at minimum deformation and the value of G' measured at the maximum deformation reached, G"$_{max}$ which is the maximum value of G" observed in the G" curve, and (tan delta)$_{max}$ which is the maximum value of tan delta observed in the curve.

The dynamic mechanical properties were further measured by application of an axial stress using an Instron dynamic device in compression-traction modality in accordance with the following methods. A sample of the crude elastomer compositions vulcanized at 170° C. for 10 minutes having a cylindrical shape (length=25 mm; diameter=14 mm), compression-preload up to 25% of the longitudinal deformation relative to the initial length and maintained at the predetermined temperature (equal to −10° C., 0° C., +23° C. or +70° C.) for the entire time length of the test, was subjected to a sinusoidal dynamic tension having an amplitude of ±3.5% relative to the length under preload, with a frequency of 10 Hz. The dynamic mechanical properties are expressed in terms of elastic dynamic modulus (F') and tan delta (dissipation factor) values. The value of Tan delta was calculated as the ratio between the viscous modulus (E") and the elastic modulus (F').

The static and dynamic mechanical properties measured are summarized in the following table 1.

TABLE 1

| Symbol | Meaning |
| --- | --- |
| Static mechanical properties | |
| $\sigma_{50}$ | Load at 50% elongation |
| $\sigma_{100}$ | Load at 100% elongation |
| $\sigma_{300}$ | Load at 300% elongation |
| $\sigma_B$ | Load at break |
| $\varepsilon_B$ | Elongation at break |
| Dynamic mechanical properties measured by means of shear stress | |
| Symbol | Meaning |
| G' | Elastic modulus |
| G" | Viscous modulus |
| tan delta | G"/G' |
| G'γ | G' at minimum deformation |
| ΔG' | G'γ - G' at maximum deformation |
| G"$_{max}$ | maximum value of G" observed |
| (tan delta)$_{max}$ | maximum value of tan delta observed |
| Dynamic mechanical properties measured by means of axial stress | |
| Symbol | Meaning |
| E' | dynamic elastic modulus |
| E" | dynamic viscous modulus |
| tan delta | dissipation factor E"/E' |

EXAMPLES

Examples 1-3: Synthesis of the Comparison Pyrrole Compounds and Those of the Invention Example 1. Synthesis of 2-(2,5-dimethyl-1H-pyrrolo-1-yl)propan-1,3-diol (Serinol Pyrrole, SP). Comparison

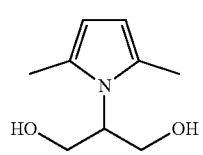

The synthesis was performed as stated in EP3209604B1, with a reaction yield of 96%.

Example 2. Synthesis of O-(2-(2,5-dimethyl-1H-pyrrol-1-yl)propyl)-O'-(2-methoxyethyl)polypropylene Glycol (PPGP). Comparison

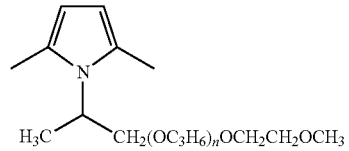

13.27 g of O-(2-aminopropyl)-O'-(2-methoxyethyl)polypropylene glycol (PPGA, 0.02212 mol), 2 g of 2,5-hexanedione (HD, 0.02212 mol) and 0.2 mL of water were poured into a 100 ml round-bottomed flask equipped with a magnetic stirrer. The mixture was then stirred (300 rpm) at ambient temperature for 12 hours. At the end of the reaction, the mixture still contained 2,5-hexanedione. The reagent was removed under reduced pressure (2 mbar, ambient temperature) using a Claisen apparatus. The pure product was obtained with a yield of 64%.

$^1$H NMR (CDCl$_3$, 400 MHz); δ (ppm)=1.13-1.15 (m, 74H); 1.47 (d, 3H); 2.25 (s, 6H); 3.32 (m, 4H); 3.32 (m, 4H); 3.42-3.78 (m, 34H); 3.66-3.5 (m, 55H); 3.74 (m, 3H); 4.35 (quintet, 1H); 5.71 (s, 2H).

Example 3. Synthesis of 2-(2,5-dimethyl-1H-pyrrol-1-yl)ethan-1-thiol (SHP). Invention

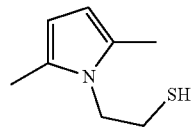

2.93 g (0.02577 mol) of 2-aminoethanethiol hydrochloride were introduced, under a constant current of N$_2$, into a 50 ml round-bottomed two-necked flask, previously dried in the oven, and the system was brought up to 50° C. with stirring (300 rpm) until complete dissolution.

The mixture was then brought back to ambient temperature, and 2.93 g (0.02577 mol) of 2,5-hexanedione were injected into the flask under a current of N$_2$. The mixture was left under stirring (300 rpm) at ambient temperature for 12 hours. Next, 1.5 g of 2-aminoethanethiol hydrochloride were added, the temperature was brought up to 50° C., and the mixture was left under stirring for one hour.

The pure product was obtained by washing with water (3×10 mL). 3.1 g of product were obtained (yield=77.5%).

$^1$H NMR (D$_2$O, 400 MHz); δ (ppm)=2.05 (s, 6H); 2.9 (m, 4H); 3.33 (t, 1H); 3.43 (t, 1H); 5.42 (s, 2H).

Examples 4-8: Preparation of the Comparison Adducts Between Carbon Allotropes and Pyrrole Derivatives and Those According to the Invention Example 4. Preparation of the Carbon Allotrope CB N234 with Serinol Pyrrole (CBN234-SP Adduct). Comparison 10 g of carbon allotrope were placed in a 250 ml round-bottomed flask and 50 mL of acetone were added so as to completely cover the black powder of the allotrope. Next, 1 g of SP was dissolved in 15 mL of acetone and added to the flask. The suspension was sonicated for 10 minutes, using a 2 litre ultrasound bath. The solvent was removed under reduced pressure using a rotary evaporator. The flask was then equipped with a magnetic stirrer and a condenser and heated to 180° C. in an oil bath; it was then left under stirring (300 rpm) for 3 hours. The reaction was therefore performed without solvents or catalysts.

Once the reaction was completed, the mixture was carefully washed with acetone leaving it under stirring at ambient temperature for one night, then placed in a Buchner funnel with a sintered glass disc, recovered and dried in the oven at 95° C.

The adduct was characterized by TGA. The weight losses determined in the ranges T<150° C., 150° C.<T<900° C., and T≥900° C. are stated in Table 1. In Table 2 the quantity by weight of SP in the adduct, expressed both in % and as phc (per hundred carbon), i.e. the parts of compound per 100 parts of carbon allotrope, and the functionalization yield values are stated.

Example 5. Preparation of the Carbon Allotrope CB N234 with PPGP (CBN234-PPGP Adduct). Comparison The procedure of example 4 was repeated, using PPGP instead of SP.

The CBN234-PPGP adduct obtained was characterized by TGA. The weight losses from TGA are stated in Table 2. In Table 3 the quantity by weight of PPGP in the adduct, expressed both in % and as phc, and the functionalization yield are stated.

Example 6. Preparation of the Carbon Allotrope CB N234 with SHP (CB N234-SHP Adduct). Invention The procedure of example 4 was repeated, using SHP instead of SP, and ethanol instead of the acetone. Once the reaction was complete, the mixture was carefully washed with acetone leaving it under stirring at ambient temperature for one night, then placed in a Buchner funnel with a sintered glass disc, recovered and dried under the hood at ambient temperature during the night.

The CBN234-SHP adduct obtained was characterized by TGA. The weight losses from TGA are shown in Table 2. In Table 3, the quantity by weight of SHP in the adduct, expressed both in % and as phc, and the functionalization yield are shown.

Example 7. Preparation of the Carbon Allotrope HSAG with PPGP (HSAG-PPGP Adduct). Comparison The procedure of example 5 was repeated using HSAG Nano27 instead of CB N234

The HSAG-PPGP adduct obtained was characterized by TGA. The weight losses from TGA are shown in Table 2. In Table 3, the quantity by weight of PPGP in the adduct, expressed both in % and as phc, and the functionalization yield are shown.

Example 8. Preparation of the Carbon Allotrope HSAG with SHP (HSAG-SHP Adduct). Comparison The procedure of example 6 was repeated using HSAG Nano27 instead of CBN234

The HSAG-SHP adduct obtained was characterized by TGA. The weight losses from TGA are shown in Table 2. In Table 3, both the quantity by weight of SHP in the adduct, expressed both in % and as phc, and the functionalization yield of the adduct, are shown.

TABLE 2

Weight losses of CB N234, HSAG Nano27 and of the adducts with pyrrole compounds

| | Weight loss [%] T < 150° C. | Weight loss [%] 150° C. < T < 900° C. | Weight loss [%] T = 900° C. |
|---|---|---|---|
| CB N234 | 0.4 | 2 | 97.6 |
| CB N234-SP | 1.1 | 7.9 | 91 |
| CB N234-PPGP | 0.9 | 8.2 | 90.9 |
| CB N234-SHP | 1 | 7.9 | 91.1 |
| HSAG (Nano27) | 0.5 | 3.6 | 95.9 |
| HSAG-PPGP | 0.2 | 9.2 | 90.6 |
| HSAG-SHP | 0.4 | 8.1 | 91.5 |

TABLE 3

| | Functionalization yield of the adducts of CB N234 and HSAG Nano27 with pyrrole compounds | |
|---|---|---|
| Adduct | phc[1] | Functionalization yield (%) |
| CBN234-SP | 5.8 | 97 |
| CBN234-PPGP | 6.3 | 95 |
| CBN234-SHP | 4.7 | 96 |
| HSAG-PPGP | 5.4 | 94 |
| HSAG-SHP | 5.6 | 93 |

[1]phc (per hundred carbon) = pars of functionalization agent relative to 100 parts of $sp^2$ carbon allotrope

Examples 9-13: Preparation of Elastomer Mixtures Comprising S-SBR and NR

Elastomer mixtures comprising the elastomers S-SBR and NR, and carbon black or mixtures of carbon black and one of the adducts between carbon black and pyrrole compounds described in the previous examples were prepared.

The following Table 4 shows the composition of the compositions obtained in examples 9-13.

As can be seen from the data shown in the tables, all the compositions obtained contain a comparable quantity of carbon black; the control compositions 10-12, comprising a mixture of CB and adduct, contain a comparable quantity of pyrrole compound which is about double compared to that of the composition of the invention (13); the ratio between carbon black and adduct in compositions 10 and 12 (control) is about 0.9, while in the compositions 11 (control) and 13 (of the invention) it is about 0.5.

TABLE 4

Composition of the compositions of examples 9-13

| | Example | | | | |
|---|---|---|---|---|---|
| | 9* | 10* | 11* | 12* | 13^ |
| | | | Carbon allotrope | | |
| | CB [phr] | CBN234-PPGP [phr] | CBN234-SP [phr] | CBN234-SP [phr] | CB N234-SHP [phr] |
| S-SBR 4630 | 70 | 70 | 70 | 70 | 70 |
| NR (SIR-20) | 30 | 30 | 30 | 30 | 30 |
| Oil | 5 | 5 | 5 | 5 | 5 |
| Wax | 1 | 1 | 1 | 1 | 1 |
| CB | 65 | 32.5 | 43.6 | 32.5 | 43.6 |
| CBN234-SHP | | | | | 22.4 |
| CBN234-PPGP | | 34.5 | | | |
| CBN234-SP | | | 22.7 | 34.3 | |
| Stearic acid | 2 | 2 | 2 | 2 | 2 |
| ZnO | 2.5 | 2.5 | 2.5 | 2.5 | 2.5 |
| 6PPD | 2 | 2 | 2 | 2 | 2 |
| TBBS | 1.8 | 1.8 | 1.8 | 1.8 | 1.8 |
| Sulphur | 1.8 | 1.8 | 1.8 | 1.8 | 1.8 |

*comparison; ^according to the invention

Example 9. Preparation of an Elastomer Composition Comprising S-SBR, NR and CB (Comparison)

S-SBR and NR were fed into a Brabender® with internal mixer and kneaded for one minute at 80° C. Then 65 phr of CB and the oil (TDAE oil, Vivatec 500) were added. After further kneading for 3 minutes, stearic acid, 6PPD and zinc oxide are added, and the composition was kneaded for another 3 minutes before discharging it. The chamber was cooled to 45° C., the composition again fed into the mixer and TBBS and sulphur were added, followed by 3 minutes of kneading. The composition was then discharged. The process was performed filling 85% of the chamber.

Example 10. Preparation of an Elastomer Composition Comprising S-SBR, NR and CBN234-PPGP. Comparison The procedure of example 9 was repeated using 32.5 phr of CB and 34.5 phr of CBN234-PPGP, instead of 65 phr of CB.

Example 11. Preparation of an Elastomer Composition Comprising S-SBR, NR and CBN234-SP. Comparison The procedure of example 9 was repeated using 43.6 phr of CB and 22.7 phr of CBN234-SP, instead of 65 phr of CB.

Example 12. Preparation of an Elastomer Composition Comprising S-SBR, NR and CBN234-SP. Comparison The procedure of example 9 was repeated using 32.5 phr of CB and 34.3 phr of CBN234-SP, instead of 65 phr of CB.

Example 13. Preparation of an Elastomer Composition Comprising S-SBR, NR and CBN234-SHP. Invention The procedure of example 9 was repeated using 43.6 phr of CB and 22.4 phr of CBN234-SHP, instead of 65 phr of CB. Further, the temperature of the mixing chamber was maintained at 45° C. for the whole process.

Vulcanization

The compositions of examples 9-13 were vulcanized at 170° C. and at the pressure of $15 \times 10^5$ Pa for 20 minutes, according to the previously described operating modalities.

In Table 5, the data relating to the vulcanization reactions are shown. In FIG. 2, the vulcanization curves are shown.

Of note in particular, the use of the adducts according to the invention leads to the reduction of the induction time of the vulcanization, compared to the composition comprising carbon black alone, particularly when the adduct CBN234-SHP is used. The values are in any case compatible with the industrial practice and relatable to typical values obtained with the use of vulcanization retardants.

TABLE 5

Values determined via the rheometer test

| | Composition | | | | |
|---|---|---|---|---|---|
| | 9* | 10* | 11* | 12* | 13^ |
| | | | Carbon allotrope | | |
| | CB | CBN234-PPGP | CBN234-SP | CBN234-SP | CBN234-SHP |
| $M_H$ [dNm] | 21.69 | 20.37 | 21.42 | 21.19 | 22.31 |
| $M_L$ [dNm] | 3.76 | 3.66 | 3.89 | 4.2 | 3.78 |
| $M_H - M_L$ [dNm] | 17.93 | 16.71 | 17.53 | 16.99 | 18.53 |
| $(M_H - M_L)/$ $(t_{90} - t_{S1})$ [dNm]/[min] | 4.79 | 5.99 | 5.45 | 5.80 | 8.09 |
| $t_{S1}$ [min] | 2.69 | 2.38 | 2.35 | 2.53 | 1.98 |
| $t_{S2}$ [min] | 3.05 | 2.63 | 2.54 | 2.75 | 2.05 |
| $t_{90}$ [min] | 6.43 | 5.17 | 5.45 | 5.46 | 4.27 |

*comparison; ^according to the invention $M_H$ maximum value of the torque, measured in dNewton × metre (dNm).
$M_L$ minimum value of the torque, measured in dNm.
$t_{S1}$: time required to have a 1 dNm increase of the torque value, relative to the minimum value $M_L$.
$t_{S2}$: time required to have a 2 dNm increase in the torque value, relative to the minimum value $M_L$.
$t_{90}$: time required to reach 90% of the torque value, relative to the maximum value $M_H$.

All the functionalized CB lead to the increase in the rate of vulcanization, calculated as $(M_H - M_L)/(t_{90} - t_{S1})$. The appreciably higher value is obtained with CBN234-SHP. No substantial reversal of the vulcanization is observed for any of the compositions. The highest value of $M_H$ and of $M_H$-$M_L$ was obtained with CBN234-SHP.

Dynamic Mechanical Characterization of the Elastomer Compositions by Means of Shear Stress The dynamic mechanical characterization was performed by applying a sinusoidal stress by means of shear stress, in accordance with the previously described operative modalities.

In Table 6, the data relating to the dynamic modulus G' at minimum deformation (0.1), to the variation of the G' modulus (ΔG') between 0.28% and 25% as deformation amplitude, to maximum value of the dissipative modulus G", and to the maximum value of tan delta are shown.

The curves of the variation in G' and of tan delta relative to the deformation amplitude are shown respectively in FIG. 3 and in FIG. 4.

TABLE 6

Values determined via the strain sweep test

| | Composition | | | | |
|---|---|---|---|---|---|
| | 9* | 10* | 11* | 12* | 13^ |
| | | Carbon allotrope | | | |
| | CB | CBN234-PPGP | CBN234-SP | CBN234-SP | CBN234-SHP |
| $G'_{max}$ | 6.13 | 6.10 | 6.07 | 5.97 | 6.36 |
| $G'_{min}$ | 1.24 | 1.22 | 1.18 | 1.28 | 1.43 |
| $\Delta G'$ | 4.89 | 4.88 | 4.89 | 4.69 | 4.94 |
| $G''_{max}$ | 0.97 | 0.97 | 0.91 | 0.90 | 0.93 |
| tan delta$_{max}$ | 0.33 | 0.33 | 0.32 | 0.31 | 0.30 |

*comparison; ^according to the invention

The compositions with CBN234-SHP show the highest value of elastic modulus G' at all the deformations, and comparable values of G" max.

The compositions with CBN234-SHP further show the lowest values of tan delta$_{max}$ and lower values of tan delta, from low to high deformations.

At the highest deformations examined, the values of tan delta for the composition comprising CBN234-SHP (13) are similar to the values of the composition 12 which contains the CBN234-SP adduct in greater quantity compared to 13 (34.3 phr compared to 22.4 phr, about 1.5:1).

Thus, the composition 13 of the invention is characterized by the lowest hysteresis and by the lowest energy dissipation.

Dynamic Mechanical Characterization of the Elastomer Compositions by Means of Axial Stress In Table 7, the data obtained from the dynamic mechanical tests, performed by application of a sinusoidal axial stress, are shown. The experimental conditions for performing the tests have been stated above. It should be emphasized that the sinusoidal stress was applied on samples compressed at 25%.

TABLE 7

| | Composition | | | |
|---|---|---|---|---|
| | 9* | 10* | 12* | 13^ |
| | | Carbon allotrope | | |
| | CB | CBN234-PPGP | CBN234-SP | CBN234-SHP |
| E' @ 10° C. | 17.52 | 16.51 | 18.28 | 19.92 |
| E" @ 10° C. | 9.74 | 9.73 | 10.19 | 10.13 |
| Tan Delta @ 10° C. | 0.56 | 0.59 | 0.56 | 0.51 |
| E' @ 23° C. | 13.18 | 12.86 | 14.10 | 15.28 |
| E" @ 23° C. | 6.02 | 6.15 | 6.47 | 6.36 |
| Tan Delta @ 23° C. | 0.46 | 0.48 | 0.46 | 0.42 |
| E' @ 70° C. | 8.18 | 8.09 | 8.40 | 9.12 |
| E" @ 70° C. | 2.06 | 2.19 | 2.17 | 2.03 |
| Tan Delta @ 70° C. | 0.25 | 0.27 | 0.26 | 0.22 |
| $\Delta E'$ (E' @ 10° C.-E' @ 70° C.) | 9.34 | 8.42 | 9.88 | 10.8 |

*comparison; ^according to the invention

The composition comprising CBN234-SHP has the highest values of E' at all the temperatures. The increase in the values of E' is greater than the increase in the values of E" at all the temperatures. Indeed, the composition comprising CBN234-SHP has the lowest values of tan delta, that is of hysteresis, at all the temperatures. The dependence of tan delta values of on the temperature is shown in FIG. 5.

Thus, while the data in Table 6 and above all the curves in FIG. 4 had shown similar values of tan delta at high deformations for the compositions with CBN234-SP and with CBN234-SHP, the data in Table 7 and in FIG. 5 clearly show that, after the application of a preload, only the composition comprising CBN234-SHP shows an appreciable reduction in the hysteresis compared to the composition comprising CB alone.

Characterization of the Elastomer Compositions by Means of Tensile Tests

In Table 8, the data obtained from the tensile tests are shown. In FIG. 6, the curves of the change in the stresses with respect to the elongations are shown.

TABLE 8

Values of the tensile properties

| | Composition | | | |
|---|---|---|---|---|
| | 9* | 10* | 12* | 13 |
| | | Carbon allotrope | | |
| | CB | CBN234-PPGP | CBN234-SP | CBN234-SHP |
| $\sigma_{50}$ (MPa) | 3.98 | 3.32 | 3.16 | 4.55 |
| $\sigma_{200}$ (MPa) | 10.70 | 9.04 | 8.14 | 11.77 |
| $\sigma_{300}$ (MPa) | 18.09 | 15.66 | 14.45 | 19.33 |
| $\sigma_{300}/\sigma_{200}$ | 1.69 | 1.73 | 1.74 | 1.64 |
| $\sigma_B$ (MPa) | 18.25 | 20.47 | 19.38 | 20.87 |
| $\varepsilon_B$ (%) | 305.35 | 391.16 | 395.12 | 326.88 |
| Energy (J/cm$^3$) | 24.71 | 36.79 | 34.82 | 31.51 |

*comparison; ^according to the invention

All the compositions with functionalized CB have values of properties at break better than the composition comprising non-functionalized CB. It should be emphasized that the composition comprising CBN234-SHP has better properties at break than the composition comprising CB alone but much higher values of loads at lower deformations, 50%, 100% and 300%, compared to all the other mixtures. Thus, the composition comprising CBN234-SHP, which has greater rigidity and less hysteresis when compared to the composition comprising CB, and to all the other mixtures, also has better properties at break than the composition comprising non-functionalized CB.

All the data collected for the compositions comprising S—SBR and NR demonstrate that the composition of the invention (13) has the best balance of all the properties: greater dynamic rigidity, less hysteresis, higher loads at low deformations, and optimal properties at break.

Examples 14-17. Preparation of the Elastomer Compositions Comprising NBR and NR

Elastomer mixtures comprising the elastomers NBR and NR, and carbon black, mixtures between carbon black/high surface area graphite, or mixtures of carbon black and one of the adducts between HSAG and pyrrole compounds described in the previous examples were prepared.

The following Table 9 shows the composition of the compositions obtained in examples 14-17. The quantity of functional group present in the compositions is indicated in Table 10.

As can be seen from the data shown in the tables, the control composition 14 contains a double quantity of carbon black compared to the others, wherein about 50% of the carbon black was replaced by HSAG (15, control) or by an adduct between HSAG and pyrrole compound (16, control, and 17, of the invention). Furthermore, both the compositions comprising an adduct between HSAG and pyrrole compound contain a comparable quantity of pyrrole compound.

TABLE 9

| | Example | | | |
|---|---|---|---|---|
| | 14* | 15* | 16* | 17 |
| | | Carbon allotrope | | |
| | CB [phr] | CB/ HSAG [phr] | CB/HSAG-PPGP [phr] | CB/HSAG-SHP [phr] |
| NBR | 70 | 70 | 70 | 70 |
| NR (SIR - 20) | 30 | 30 | 30 | 30 |
| PPGP | 4 | 4 | 4 | 4 |
| CB | 60 | 30 | 30 | 30 |
| HSAG | | 30 | | |
| HSAG-PPGP | | | 31.6 | |
| HSAG-SHP | | | | 31.6 |
| Stearic acid | 2 | 2 | 2 | 2 |
| ZnO | 5 | 5 | 5 | 5 |
| Agerite Resin D | 1 | 1 | 1 | 1 |
| CBS | 1.5 | 1.5 | 1.5 | 1.5 |
| Sulphur | 1.5 | 1.5 | 1.5 | 1.5 |

*comparison; ^according to the invention

TABLE 10

Quantity of functional groups in the elastomer compositions

| | Example | |
|---|---|---|
| | 16* | 17 |
| | Carbon allotropes | |
| | CB/HSAG-PPGP | CB/HSAG-SHP |
| phr | 1.56 | 1.59 |

*comparison; ^according to the invention

Example 14. Preparation of an Elastomer Composition Comprising NBR, NR and CB. Comparative Example NBR and NR were fed into a Brabender®, with internal mixer, and kneaded for one minute at 85° C. Then the paraffin oil was added. After further kneading for 3 minutes, stearic acid, Agerite Resin D and zinc oxide were added, and the composition was kneaded for another 3 minutes before discharging it. The chamber was cooled to 45° C., the composition fed again into the mixer and CBS and sulphur were added, followed by 3 minutes of kneading. The composition was then discharged. The process was performed filling 85% of the chamber.

Example 15. Preparation of an Elastomer Composition Comprising NBR, NR, CB and HSAG. Comparative Example The procedure of example 14 was repeated using a CB/HSAG mixture (50/50 by weight) instead of CB.

Example 16. Preparation of an Elastomer Composition Comprising NBR, NR, CB and HSAG-PPGP. Comparative Example The procedure of example 14 was repeated using a mixture of CB and adduct HSAG-PPGP (CB/HSAG ratio=50/50 by weight) instead of CB.

Example 17. Preparation of an Elastomer Composition Comprising NBR, NR, CB and HSAG-SHP. Example of the Invention The procedure of example 14 was repeated using a mixture of CB and adduct HSAG-SHP (CB/HSAG ratio=50/50 by weight) instead of CB. Further, the temperature of the chamber was maintained at 45° C. for the whole process.

Vulcanization of the Elastomer Compositions

The compositions of examples 14-17 were vulcanized at 170° C. and at the pressure of $15 \times 10^5$ Pa for 20 minutes, in accordance with the previously described operating modalities.

In Table 11, the data of the vulcanization reactions are shown. In FIG. 7, the vulcanization curves are shown.

TABLE 11

Values determined via the rheometer test

| | Composition | | | |
|---|---|---|---|---|
| | 14* | 15* | 16* | 17 |
| | | Carbon allotrope | | |
| | CB | CB/ HSAG | CB/HSAG-PPGP | CB/HSAG-SHP |
| $M_H$ [dNm] | 21.22 | 15.95 | 14.71 | 18.58 |
| $M_L$ [dNm] | 3.31 | 2.67 | 2.42 | 2.37 |
| $M_H - M_L$ [dNm] | 17.91 | 13.28 | 12.29 | 16.21 |
| $t_{90}$ [Min] | 4.24 | 6.28 | 6.14 | 4.44 |

*comparison; ^according to the invention

The replacement of CB with HSAG and HSAG-PPGP leads to the increase of the vulcanization induction time and to a reduction in the rate of vulcanization as indicated by the slope of the curve between the induction and the plateau in FIG. 7. By contrast, using the adduct HSAG-SHP the same vulcanization behaviour observed for the composition 14, comprising CB alone, is obtained.

The values of $M_L$ are lower in the case of the compositions with HSAG, as such or functionalized. The lowest value is obtained with HSAG-SHP.

Hence the adducts according to the invention impart advantageous properties to the elastomer mixtures even when a carbon allotrope different from CB is used.

Dynamic Mechanical Characterization of the Elastomer Compositions by Means of Shear Stress The dynamic mechanical characterization was performed applying a sinusoidal stress by means of shear stress, in accordance with the previously described operative modalities.

Table 12 shows the data relating to the dynamic modulus G' at minimum deformation (0.1%), to the variation Δ in the G' modulus (ΔG') between 0.28% and 25% as deformation amplitude, to the maximum value of the dissipative modulus G", and to the maximum value of tan delta.

FIG. 8 shows the curves for tan delta variation relative to the deformation amplitude.

TABLE 12

| | Composition | | | |
|---|---|---|---|---|
| | 14* | 15* | 16* | 17 |
| | | Carbon allotrope | | |
| | CB | CB/HSAG | CB/HSAG-PPGP | CB/HSAG-SHP |
| $G'_{min}$ | 8.72 | 5.49 | 5.23 | 5.27 |
| $G'_{max}$ | 1.78 | 1.44 | 1.35 | 1.54 |
| $\Delta G'$ | 6.94 | 4.06 | 3.89 | 3.73 |
| $G''_{max}$ | 1.29 | 0.82 | 0.81 | 0.77 |
| Tan Delta$_{max}$ | 0.34 | 0.30 | 0.31 | 0.27 |

*comparison; ^according to the invention

The G' values of the compositions comprising HSAG, as such or functionalized, are lower than the G' values of the composition comprising CB alone.

The composition comprising HSAG-SHP shows the lowest value of G' at minimum deformation, and, among the compositions comprising HSAG, the highest value of G' at high strain.

These are positive data, since they indicate that HSAG-SHP leads to the smallest Payne effect. Indeed, the value of $\Delta G'$ is appreciably lower for the composition comprising HSAG-SHP.

The composition comprising HSAG-SHP also has lower values of G" max.

Finally, the composition comprising HSAG-SHP has the lowest values of tan delta over the whole amplitude of deformation, as can be observed in FIG. 8. This means that the composition comprising HSAG-SHP has the smallest hysteresis, hence the smallest energy dissipation.

Dynamic Mechanical Characterization of the Elastomer Compositions by Means of Axial Stress The data obtained from the dynamic mechanical tests, performed applying a sinusoidal axial stress, are shown in Table 13. The experimental conditions for performing the tests have been described above. It should be emphasized that the sinusoidal stress was applied on samples compressed at 25%.

TABLE 13

| | Composition | | | |
|---|---|---|---|---|
| | 14* | 15* | 16* | 17 |
| | | Carbon allotrope | | |
| | CB | CB/HSAG | CB/HSAG-PPGP | CB/HSAG-SHP |
| E' @ 10° C. | 27.15 | 27.84 | 27.28 | 28.93 |
| E" @ 10° C. | 12.33 | 11.69 | 11.75 | 12.34 |
| Tan Delta @ 10° C. | 0.45 | 0.42 | 0.43 | 0.43 |
| E' @ 23° C. | 22.51 | 22.86 | 22.29 | 23.75 |
| E" @ 23° C. | 8.66 | 7.82 | 7.80 | 8.14 |
| Tan Delta @ 23° C. | 0.39 | 0.34 | 0.35 | 0.34 |
| E' @ 70° C. | 12.70 | 13.78 | 13.28 | 14.55 |
| E" @ 70° C. | 3.73 | 3.46 | 3.46 | 3.40 |
| Tan Delta @ 70° C. | 0.29 | 0.25 | 0.26 | 0.23 |
| $\Delta E'$ (E' @ 10° C.-E' @ 70° C.) | 14.44 | 14.06 | 14.01 | 14.38 |

*comparison; ^according to the invention

The composition of the invention, comprising HSAG-SHP, shows the highest values of E' at all the temperatures, hence greater dynamic rigidity. This composition also shows, at all the temperatures, tan delta values lower than those of the composition comprising CB alone and, at low temperatures, in line with the values of the compositions comprising HSAG and HSAG-PPGP.

The tan delta value for the composition comprising HSAG-SHP is the lowest at medium-high temperature (70° C.). This data is certainly positive since the tan delta at medium-high temperature is indicative of the energy dissipation of a composition for tyres under normal use conditions.

Characterization of the Elastomer Compositions by Means of Tensile Tests

The data obtained in the tensile tests are shown in Table 14.

TABLE 14

| | Composition | | | |
|---|---|---|---|---|
| | 14* | 15* | 16* | 17 |
| | | Carbon allotrope | | |
| | CB | CB/HSAG | CB/HSAG-PPGP | CB/HSAG-SHP |
| $\sigma_{50}$ (MPa) | 3.59 | 5.17 | 4.38 | 6.71 |
| $\sigma_{200}$ (MPa) | 8.32 | 9.45 | 8.09 | 12.83 |
| $\sigma_{300}$ (MPa) | 14.34 | 13.32 | 11.63 | 17.65 |
| $\sigma_{300}/\sigma_{200}$ | 1.72 | 1.41 | 1.44 | 1.38 |
| $\sigma_B$ (MPa) | 19.82 | 19.18 | 18.44 | 19.69 |
| $\varepsilon_B$ (%) | 406.94 | 489.53 | 523.93 | 351.48 |
| Energy (J/cm$^3$) | 37.79 | 52.93 | 52.89 | 38.53 |

*comparison; ^according to the invention

The composition comprising HSAG-SHP clearly shows the highest reinforcement values up to 300% elongation. Furthermore, it shows load at break and energy at break values which are in line with or higher when compared to the composition comprising CB alone.

In conclusion, the composition comprising the hybrid filler system CB/HSAG-SHP shows the lowest hysteresis, that is the least energy dissipation, particularly under the normal use conditions for a tyre and has, at the same time, vulcanization and static reinforcement parameters in line with those of a reference composition comprising CB alone.

The invention claimed is:

1. An adduct between an sp$^2$ hybridized carbon allotrope and a pyrrole derivative, wherein the pyrrole derivative is represented by formula (1)

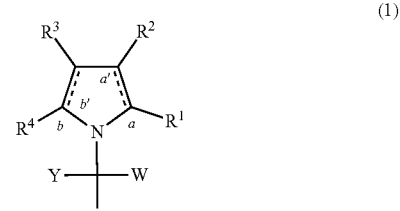

(1)

wherein
R$_1$, R$_2$, R$_3$, and R$_4$ are independently chosen from: hydrogen, linear or branched C$_1$-C$_{22}$ alkyl, linear or branched C$_2$-C$_{22}$ alkenyl or alkynyl, aryl, linear or branched C$_1$-C$_{22}$ alkyl-aryl, linear or branched C$_2$-C$_{22}$ alkenyl-aryl, linear or branched C$_2$-C$_{22}$ alkynyl-aryl, and heteroaryl;
the dashed lines (a') and (b') independently represent a double bond or a single bond; and W, Y and Z are independently chosen from: hydrogen, linear or branched $C_1$-$C_{18}$ alkyl, linear or branched $C_2$-$C_{18}$ alkenyl or alkynyl, and formulae (II)-(V) depicted below

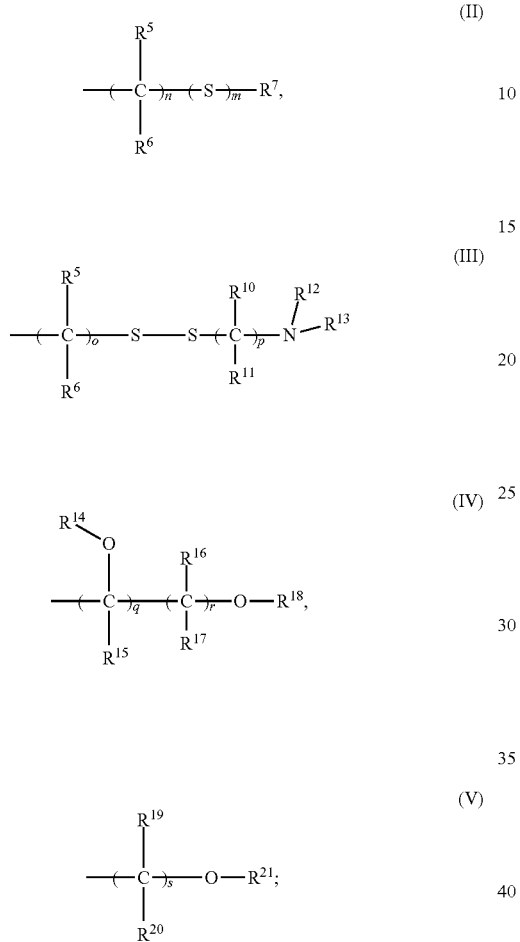

wherein $R_5$, $R_6$, $R_7$, $R_8$, $R_9$, $R_{10}$, $R_{11}$, $R_{12}$, $R_{13}$, $R_{14}$, $R_{15}$, $R_{16}$, $R_{17}$, $R_{18}$, $R_{19}$, $R_{20}$, and $R_{21}$ are independently chosen from: hydrogen, linear or branched $C_1$-$C_{18}$ alkyl, linear or branched $C_2$-$C_{18}$ alkenyl or alkynyl, aryl, linear or branched $C_1$-$C_{22}$ alkyl-aryl, linear or branched $C_2$-$C_{22}$ alkenyl-aryl, linear or branched $C_2$-$C_{22}$ alkynyl-aryl, heteroaryl, carboxyl, acyl-alkyl with linear or branched $C_1$-$C_{18}$ alkyl, acyl-alkenyl or acyl-alkynyl with linear or branched $C_2$-$C_{18}$ alkenyl and alkynyl, acyl-aryl, acyl-heteroaryl, and acyl-amine, wherein the aryl and heteroaryl groups are optionally substituted by one or more groups chosen from $C_1$-$C_3$ alkyl, carboxyl, and acyl-alkyl with $C_1$-$C_3$ alkyl;

or $R_{12}$ and $R_{13}$ together form a pyrrole ring optionally substituted by one or more $C_1$-$C_3$ alkyl groups;

and wherein m is an integer ranging from 1 to 4, and n, o, p, q, r, and s are, independently of one another, an integer ranging from 1 to 12;

and wherein when both the dashed lines (a') and (b') represent a double bond, then formula (1) is represented by formula (1a) wherein $R_1$-$R_4$ and W, Y, and Z have the meanings stated above, and wherein at least one among W, Y, and Z is represented by one of formulae (II)-(III) above:

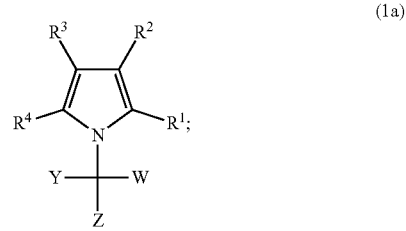

or when only the dashed line (b') represents a double bond, then Y is hydrogen, W is a —$CH_2$—S— group which together with the carbon in position "a" forms a 5-membered ring, and formula (1) is represented by formula (1b) below wherein $R_1$-$R_4$ and Z have the meanings stated above:

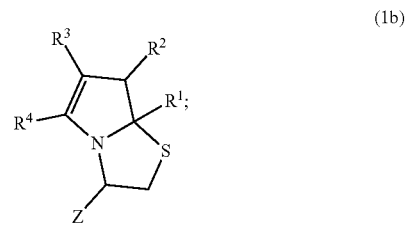

or when both the dashed lines represent a single bond, then Y and W are both a —$CH_2$—S— group, and each of together with the carbons in position "a" and "b" forms a 5-membered ring, and formula (1) is represented by formula (1c) wherein $R_1$-$R_4$ and Z have the meanings stated above:

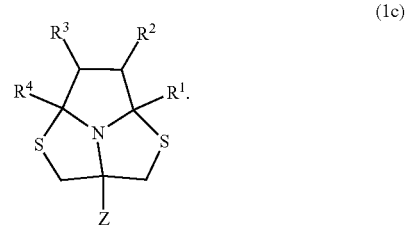

2. The adduct according to claim 1, wherein the $sp^2$ hybridized carbon allotrope is chosen from: carbon black, graphene, 2 layer graphene, from 3 to 10 layer graphene, graphite, high surface area graphite, single wall or multiwall carbon nanotubes, carbon nanotubes of longitudinal or helicoid extension, nanocones, nanohorns, nanotoroids, fullerene, and mixtures thereof.

3. The adduct according to claim 2, wherein the $sp^2$ hybridized carbon allotrope is chosen from carbon black, graphene, graphite, high surface area graphite, single wall or multiwall carbon nanotubes, and mixtures thereof.

4. The adduct according to claim 2, wherein the $sp^2$ hybridized carbon allotrope is carbon black, high surface area graphite, or mixtures thereof.

5. The adduct according to claim 1, wherein the pyrrole derivative is represented by formula (1a)

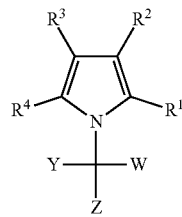

(1a)

wherein
$R_1$, $R_2$, $R_3$, and $R_4$ are independently chosen from: hydrogen, linear or branched $C_2$-$C_{22}$ alkyl, linear or branched $C_2$-$C_{22}$ alkenyl or alkynyl, aryl, linear or branched $C_1$-$C_{22}$ alkyl-aryl, linear or branched $C_2$-$C_{22}$ alkenyl-aryl, linear or branched $C_2$-$C_{22}$ alkynyl-aryl, and heteroaryl;
W, Y and Z are independently chosen from: hydrogen, linear or branched $C_1$-$C_{18}$ alkyl and linear or branched $C_2$-$C_{18}$ alkenyl or alkynyl, and formulae (II)-(V) depicted below:

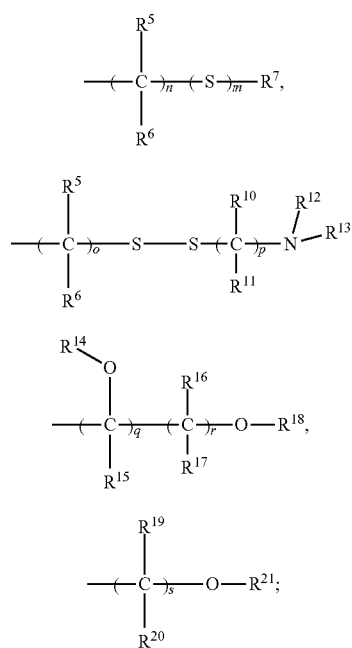

wherein $R_5$, $R_6$, $R_7$, $R_8$, $R_9$, $R_{10}$, $R_{11}$, $R_{12}$, $R_{13}$, $R_{14}$, $R_{15}$, $R_{16}$, $R_{17}$, $R_{18}$, $R_{19}$, $R_{20}$, and $R_{21}$ are independently chosen from: hydrogen, linear or branched $C_1$-$C_{18}$ alkyl, linear or branched $C_2$-$C_{18}$ alkenyl or alkynyl, aryl, linear or branched $C_1$-$C_{22}$ alkyl-aryl, linear or branched $C_2$-$C_{22}$ alkenyl-aryl, linear or branched $C_1$-$C_{22}$ alkynyl-aryl, heteroaryl, carboxyl, acyl-alkyl with linear or branched $C_1$-$C_{18}$ alkyl, acyl-alkenyl or acyl-alkynyl with linear or branched $C_1$-$C_{18}$ alkenyl and alkynyl, acyl-aryl, acyl-heteroaryl, and acyl-amine, wherein the aryl and heteroaryl groups are optionally substituted by one or more groups chosen from $C_1$-$C_3$ alkyl, carboxyl, and acyl-alkyl with $C_1$-$C_3$ alkyl;
or $R_{12}$ and $R_{13}$ together form a pyrrole ring optionally substituted by one or more $C_1$-$C_3$ alkyl groups;
and wherein m is an integer ranging from 1 to 4, and n, o, p, q, and r, and s are, independently of one another, an integer ranging from 1 to 12;
and wherein at least one among W, Y, and Z is represented by one of formulae (II)-(III) above.

6. The adduct according to claim 5, wherein the pyrrole derivative is represented by formula (1a)

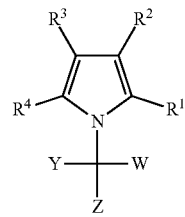

(1a)

wherein
$R_1$, $R_2$, $R_3$, and $R_4$ are independently chosen from: hydrogen, linear or branched $C_1$-$C_{22}$ alkyl, linear or branched $C_2$-$C_{22}$ alkenyl or alkynyl, aryl, linear or branched $C_1$-$C_{22}$ alkyl-aryl, linear or branched $C_2$-$C_{22}$ alkenyl-aryl, linear or branched $C_2$-$C_{22}$ alkynyl-aryl, and heteroaryl;
W and Y are independently chosen from: hydrogen, linear or branched $C_1$-$C_{18}$ alkyl, linear or branched $C_2$-$C_{18}$ alkenyl or alkynyl; and
Z is represented by one of formulae (II)-(III) stated below:

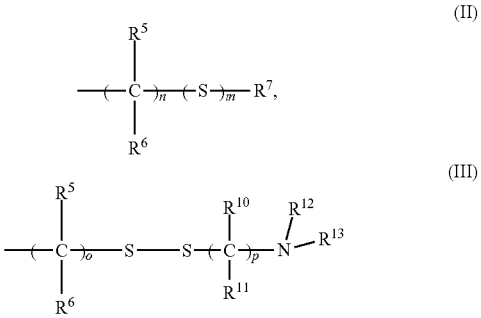

wherein $R_5$, $R_6$, $R_7$, $R_8$, $R_9$, $R_{10}$, $R_{11}$, $R_{12}$, and $R_{13}$ are independently chosen from:
hydrogen, linear or branched $C_1$-$C_{18}$ alkyl, linear or branched $C_2$-$C_{18}$ alkenyl or alkynyl, aryl, linear or branched $C_1$-$C_{22}$ alkyl-aryl, linear or branched $C_2$-$C_{22}$ alkenyl-aryl, linear or branched $C_2$-$C_{22}$ alkynyl-aryl, heteroaryl, carboxyl, acyl-alkyl with linear or branched $C_1$-$C_{18}$ alkyl, acyl-alkenyl or acyl-alkynyl with linear or branched $C_2$-$C_{18}$ alkenyl and alkynyl, acyl-aryl, acyl-heteroaryl, and acyl-amine, wherein the aryl and heteroaryl groups are optionally substituted by one or more groups chosen from $C_1$-$C_3$ alkyl, carboxyl, and acyl-alkyl with $C_1$-$C_3$ alkyl;
or $R_{12}$ and $R_{13}$ together form a pyrrole ring optionally substituted by one or more $C_1$-$C_3$ alkyl groups;
and wherein m is an integer ranging from 1 to 4, and n, o, and p are, independently of one another, an integer ranging from 1 to 12.

7. The adduct according to claim 6, wherein the pyrrole derivative is represented by formula (1a)

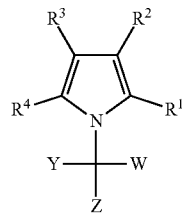

wherein $R_1$, $R_2$, $R_3$, and $R_4$ are independently chosen from: hydrogen and linear or branched $C_1$-$C_3$ alkyl;

W and Y are independently chosen from: hydrogen and linear or branched $C_1$-$C_3$ alkyl; and Z is represented by one of formulae (II)-(III) stated below:

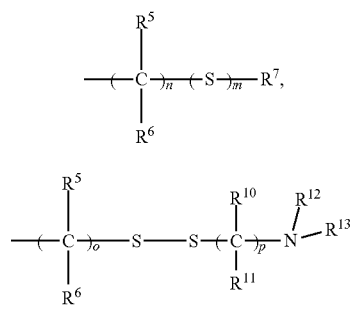

wherein $R_5$, $R_6$, $R_7$, $R_8$, $R_9$, $R_{10}$, and $R_{11}$ are represented by hydrogen or linear or branched $C_1$-$C_3$ alkyl; and $R_7$, $R_{12}$ and $R_{13}$ are independently chosen from: hydrogen, linear or branched $C_1$-$C_{18}$ alkyl, acyl-alkyl with linear or branched $C_1$-$C_{18}$ alkyl, acyl-alkenyl with linear or branched $C_2$-$C_{18}$ alkenyl, and acyl-aryl, wherein the aryl group is optionally substituted by one or more carboxyl groups;

or $R_{12}$ and $R_{13}$ together form a pyrrole ring optionally substituted by one or more $C_1$-$C_3$ alkyl groups;

and wherein m is 1, and n, o, and p are, independently of one another, an integer ranging from 1 to 4.

8. A process for the preparation of an adduct comprising the steps of:
  a) forming a mixture of at least one compound of formula (1) defined in claim 1 and at least one sp² hybridized carbon allotrope; and
  b) supplying energy to the mixture obtained in step a) to obtain an adduct.

9. The process according to claim 8, wherein the energy supplied in step b) is chosen from mechanical energy, thermal energy, and energy by irradiation with photons, or a combination thereof.

10. The process according to claim 8, further comprising the steps of:
  i) obtaining a solution of at least one compound of formula (1) in a polar protic or aprotic solvent chosen from: water, alcohols, carbonyl solvents, dimethyl sulfoxide, acetonitrile, ethers, or mixtures thereof;
  ii) obtaining a suspension of the carbon allotrope in the polar protic or aprotic solvent used for the preparation of the solution in step i);
  iii) mixing the solution and the suspension by mechanical or magnetic stirring, or by sonication;
  iv) removing the solvent from the mixture obtained in step iii); and
  v) supplying energy chosen from thermal energy, mechanical energy, energy by irradiation with photons, and combinations thereof, to the mixture obtained in step iv), in the presence of air or oxygen.

11. A crosslinkable elastomer composition comprising an adduct between an sp² hybridized carbon allotrope and a pyrrole derivative according to claim 1.

12. The crosslinkable elastomer composition according to claim 11, wherein an amount of adduct ranging from 5 to 100 phr.

13. The crosslinkable elastomer composition according to claim 11, further comprising additional reinforcing fillers chosen from: carbon black, silica, layered silicates, mixed oxides of aluminium and magnesium with lamellar structure, alumina, and silico aluminates.

14. A tyre for vehicle wheels comprising at least one structural element comprising a crosslinked elastomer material obtained by crosslinking of a crosslinkable elastomer composition according to claim 11.

15. The tyre according to claim 14, wherein the structural element is chosen from: tread band, sidewall, sidewall insert, layers of elastomer material radially internal relative to said tread band, and wherein the radially internal layers are chosen from: cushion and mini-sidewall, bead structures, and rubber coating of the textiles and the metals.

* * * * *